United States Patent
Wingenter et al.

(10) Patent No.: US 10,431,035 B2
(45) Date of Patent: Oct. 1, 2019

(54) PICKING DEVICE AND METHOD FOR RETRIEVING DRUG COMPOSITIONS FROM STORAGE

(71) Applicant: Becton Dickinson Rowa Germany GmbH, Kelberg (DE)

(72) Inventors: Dirk Wingenter, Daun (DE); Christoph Hellenbrand, Kaifenheim (DE)

(73) Assignee: BECTON DICKINSON ROWA GERMANY GMBH, Kelberg (DE)

( * ) Notice: Subject to any disclaimer, the term of this patent is extended or adjusted under 35 U.S.C. 154(b) by 106 days.

(21) Appl. No.: 15/666,109

(22) Filed: Aug. 1, 2017

(65) Prior Publication Data
US 2019/0042701 A1    Feb. 7, 2019

(51) Int. Cl.
| | |
|---|---|
| G07F 11/16 | (2006.01) |
| G07F 17/00 | (2006.01) |
| G07F 11/46 | (2006.01) |
| B65C 3/08 | (2006.01) |
| B65B 5/08 | (2006.01) |
| B65B 5/06 | (2006.01) |
| G07F 11/60 | (2006.01) |
| G07F 11/62 | (2006.01) |
| G16H 20/13 | (2018.01) |
| A61J 1/00 | (2006.01) |

(52) U.S. Cl.
CPC ............ *G07F 17/0092* (2013.01); *B65B 5/06* (2013.01); *B65B 5/08* (2013.01); *B65C 3/08* (2013.01); *G07F 11/165* (2013.01); *G07F 11/46* (2013.01); *G07F 11/60* (2013.01); *G07F 11/62* (2013.01); *A61J 1/00* (2013.01); *G16H 20/13* (2018.01)

(58) Field of Classification Search
CPC .............................. G07F 11/165; G07F 11/46
See application file for complete search history.

(56) References Cited

U.S. PATENT DOCUMENTS

| | | | | |
|---|---|---|---|---|
| 4,867,628 A | * | 9/1989 | Ammon ................ | G07F 11/165 414/273 |
| 6,735,497 B2 | * | 5/2004 | Wallace ................ | G06F 19/326 700/231 |
| 7,228,198 B2 | * | 6/2007 | Vollm ..................... | B65B 5/103 700/228 |
| 7,673,772 B2 | * | 3/2010 | Bedore ................... | G07F 11/56 221/1 |

(Continued)

FOREIGN PATENT DOCUMENTS

| | | |
|---|---|---|
| DE | 4336885 A1 | 4/1995 |
| DE | 29515627 U1 | 12/1995 |
| EP | 0909725 A2 | 4/1999 |

OTHER PUBLICATIONS

Translation of International Search Report for Application No. PCT/EP2018/067836, dated Aug. 6, 2018, 2 pages.

*Primary Examiner* — Thomas Randazzo
(74) *Attorney, Agent, or Firm* — Morgan, Lewis & Bockius LLP

(57) ABSTRACT

A picking device for dispensing drug combinations arranged in storage vessels is provided. A storage device includes multiple storage locations for storage vessels, and an operating device is coupled to a controller. A stocking device moves storage vessels into the storage device, and an unloading device transfers drug combinations arranged in the storage vessels to a transport device.

25 Claims, 10 Drawing Sheets

(56) References Cited

U.S. PATENT DOCUMENTS

| | | | | |
|---|---|---|---|---|
| 7,853,355 | B1* | 12/2010 | Willemse | G07F 9/026 700/232 |
| 8,019,470 | B2* | 9/2011 | Meek, Jr. | E05B 47/0002 700/232 |
| 8,914,298 | B1* | 12/2014 | Luciano | B65B 61/26 705/2 |
| 9,280,863 | B2* | 3/2016 | Spignesi, Jr. | G06F 19/3462 |
| 9,691,114 | B2* | 6/2017 | Ashrafzadeh | G06F 19/3462 |
| 9,937,100 | B1* | 4/2018 | Joplin | B65C 3/08 |
| 2002/0173875 | A1* | 11/2002 | Wallace | G06F 19/326 700/242 |
| 2007/0010910 | A1* | 1/2007 | Pinney | G06F 19/3462 700/231 |
| 2010/0268380 | A1* | 10/2010 | Waugh | G07F 11/44 700/239 |
| 2011/0054668 | A1* | 3/2011 | Holmes | G06Q 20/40145 700/216 |
| 2013/0092700 | A1* | 4/2013 | Braunstein | G07F 9/006 221/13 |
| 2014/0094960 | A1* | 4/2014 | Holmes | G07F 17/0092 700/216 |
| 2015/0127145 | A1* | 5/2015 | Kim | G06F 19/3462 700/235 |
| 2015/0274333 | A1* | 10/2015 | Greyshock | B65B 57/12 53/473 |
| 2017/0053099 | A1* | 2/2017 | Coughlin | G06F 19/3462 |
| 2017/0065488 | A1* | 3/2017 | Thach | A61J 7/0481 |
| 2017/0107005 | A1* | 4/2017 | Joplin | B65B 35/26 |
| 2017/0217619 | A1* | 8/2017 | Hellenbrand | B65B 35/30 |

* cited by examiner

PICKING DEVICE AND METHOD FOR RETRIEVING DRUG COMPOSITIONS FROM STORAGE

BACKGROUND

The present disclosure relates to a picking device for dispensing drug combinations, and in particular to a picking device for dispensing drug combinations arranged in storage vessels.

Automated picking devices are frequently used in pharmacies to store drug packages in a manner which saves space and which enables rapid dispensing. The drug packages are chaotically stored in the known picking devices which are particularly suitable for pharmacies. This means that the drug packs are stored not in predetermined storage locations in the device, but rather in storage locations where there is sufficient space at the moment. The picking devices operating according to the principle of chaotic storage are limited to a special type of drug packs suitable for the operating devices and for the storage spaces used in the picking devices. However, sometimes a patient is to be prescribed patient-specific drug combinations that include a precisely predetermined number of drugs of certain types, which are compiled by authorized personnel in a pharmacy, for example, and are subsequently placed in storage pouches until collected by a patient. Since patient-specific drug combinations are prepared for each patient, it is essential in such a system that a storage pouch clearly represents the drug combination placed in the same pouch, and that there is a link between the storage pouch and the drug combination. For this purpose, a corresponding identifier (e.g., a barcode) is affixed to the storage pouches. However, such a system is mechanically complex, and this mechanical complexity results in low dispensing speeds and increased maintenance efforts.

SUMMARY

In one or more embodiments, a picking device for dispensing drug combinations arranged in storage vessels includes at least one storage device having a plurality of storage locations for storage vessels and an operating device configured to be moved horizontally and vertically in front of a row of shelves, the operating device coupled to a control device. The picking device also includes at least one stocking device configured to move storage vessels for drug combinations into the storage device, wherein the operating device is configured to remove the storage vessels therefrom, and at least one first identifying device for identifying the drug combinations. The picking device further includes an unloading device and at least one delivery station coupled to the control device, the delivery station comprising a removal location and a user interface. The picking device also includes a transport device, coupled to the control device, configured to transfer drug combinations from the unloading device, wherein the transport device connects the storage device to each of the at least one delivery stations, and wherein any of the drug combinations is deliverable to any of the at least one delivery stations.

In one or more embodiments, a method for retrieving drug combinations arranged in storage vessels in a picking device includes a) identifying a drug combination to be retrieved, the identifying including providing, by a user, uniquely identifying identification data for the drug combination to be retrieved and determining a storage location inside the picking device assigned to the drug combination to be retrieved. The method also includes b) moving an operating device to the assigned storage location of the drug combination and c) gripping, by the operating device, a storage vessel arranged at the assigned storage location, the storage vessel containing the drug combination, and transferring the storage vessel to a vessel receptacle of an unloading device. The method further includes d) emptying the transferred storage vessel onto the transport device and e) transporting, by the transport device, the drug combination to a removal location of a delivery station. The method also includes f) clearing the removal location of the drug combination upon instructions from a control device coupled to the delivery station.

BRIEF DESCRIPTION OF THE DRAWINGS

The device according to the present disclosure and the method according to the present disclosure are described in greater detail below, with reference to the appended drawings, wherein:

FIGS. 13*b* and 13*c* are schematic views of the storage vessel in FIG. 13*a* during a filling process and an unloading process;

DETAILED DESCRIPTION

Figure 1:
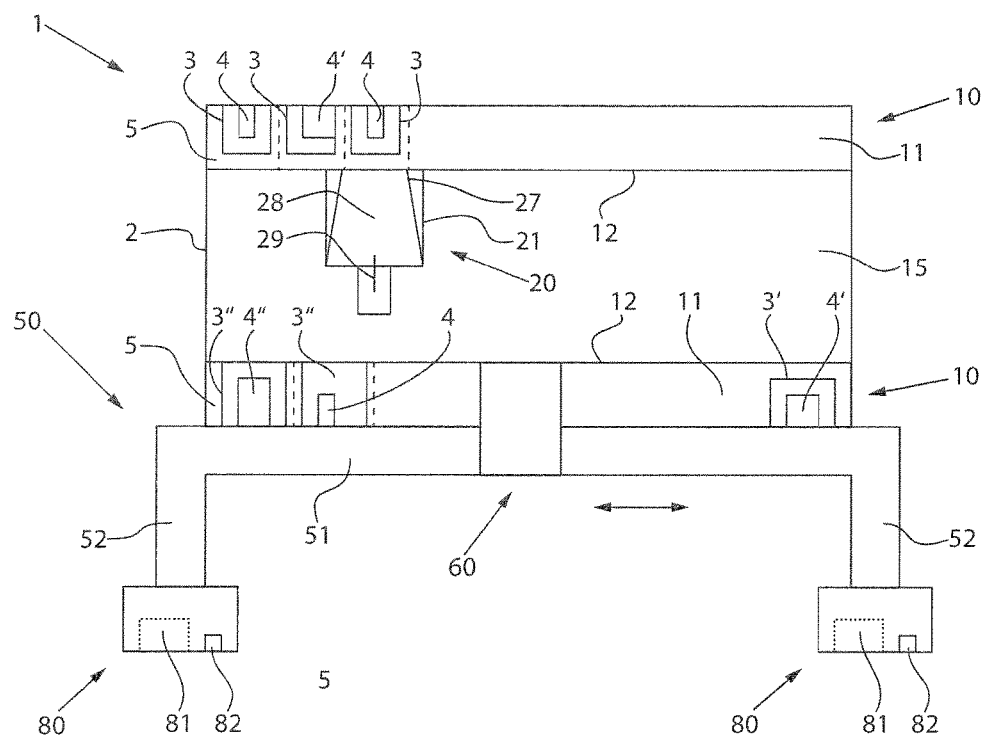
FIG. 1 is a top view of one or more embodiments of a picking device.

The present disclosure provides a picking device for dispensing drug combinations arranged in storage vessels.

In the scope of this application, the term "drug combination" always refers to the plural as well. Therefore, where a "drug combination" is mentioned, this can also mean several drug combinations (to the extent that this makes sense in the context).

One or more embodiments provide a controller for a commissioning device with horizontal storage surfaces for storing piece goods. Many controllers have numerous components which are necessary to execute the pivoting motion, which leads to high costs for the controller. Furthermore, the design of the guide and the translation of a rotational motion of a drive into the pivoting motion of the clamping jaws limit the jaws to exert only a limited clamping force onto piece goods to be retrieved. Medicinal packages are changing is size, and an increasing number of medicinal packages with larger dimensions and higher weights are appearing on the market such that increased clamping force has become desirable.

In some embodiments described herein, the controller includes a delivery table extending in a first horizontal direction, the delivery table having a storage end and a retrieval end, two elongated clamping jaws disposed above the delivery table and comprising clamping surfaces facing one another, and a clamping jaw guide apparatus. The clamping jaw guide apparatus includes a frame structure and at least one first and one second guide that are parallel and apart from one another in the first horizontal direction and extend in a second horizontal direction perpendicular to the first horizontal direction. The clamping jaw guide apparatus also includes at least four clamping jaw carriages coupled to the guides and driven in the second horizontal direction, wherein two first clamping jaw carriages are associated with the first guide and two second clamping jaw carriages are associated with the second guide, respectively, and wherein at least two clamping jaw carriages separated from one another in the first horizontal direction are coupled to a single clamping jaw, respectively. The controller further includes a guide apparatus drive unit coupled to the clamping jaw guide apparatus, the guide apparatus drive unit configured to drive the clamping jaw guide apparatus in the first horizontal direction.

One or more disclosed embodiments provide a controller having a delivery table, a plurality of elongated clamping jaws disposed above the delivery table, and a clamping jaw guide apparatus. The clamping jaw guide apparatus includes a frame structure, a plurality of guides disposed in parallel with the frame structure, and a plurality of clamping jaw carriages coupled to the plurality of guides, the plurality of clamping jaw carriages configured to be driven in parallel with the frame structure. Each of the plurality of guides is associated with one or more of the plurality of clamping jaw carriages and at least two of the plurality of clamping jaw carriages are coupled to each of the plurality of clamping jaws. The controller also includes a guide apparatus drive unit coupled to the clamping jaw guide apparatus, the drive unit configured to drive the clamping jaw guide apparatus along the delivery table. First clamping jaw carriages are associated with the first guide and second clamping jaw carriages are associated with the second guide. At least two of the plurality of clamping jaw carriages are coupled to one of the clamping jaws and are separated from one another in the first direction.

One or more disclosed embodiments provide a commissioning device controller having a delivery table elongated in a first direction, two clamping jaws disposed above the delivery table, a guide apparatus drive unit, and a clamping jaw guide apparatus coupled to the guide apparatus drive unit. The guide apparatus drive unit is configured to drive the clamping jaw guide apparatus in the first direction. The clamping jaw guide apparatus includes a frame structure, first and second guides disposed in parallel and apart from one another along the first direction, and extending in a second direction perpendicular to the first direction, and a plurality of clamping jaw carriages coupled to the first and second guides and configured to be moveable in the second direction.

For example, a picking device may include at least one storage device with a plurality of storage locations for storage vessels, an operating device which can be moved horizontally and vertically in front of the row of shelves and is coupled to a control device, at least one stocking device used to move storage vessels for drug combinations into the storage device, wherein the operating device can remove storage vessels from said stocking device, and at least one first identifying device for identifying drug combinations. The above-mentioned components of the picking device form the central storage area for the storage vessels holding drug combinations. The device described above can correspond to storage devices already known from the prior art as far as the aforementioned features are concerned.

The storage locations may be furnished, by way of example, by at least one row of shelves with a plurality of shelves arranged one above the other, each extending in a plane, wherein the storage locations are formed on the shelves. The storage locations may also be provided by simple struts, wherein a storage vessel is typically held by two struts. Depending on the requirements for warehousing and disposal, the two aforementioned ways of furnishing storage locations may also be combined. In the following, it is assumed that the storage locations are furnished by shelves.

The storage device of the picking device further includes an unloading device, with which drug combinations arranged in storage vessels are transferred to a transport device coupled to the control device.

In the picking device, drugs are not stored in drug packs directly on the shelves. Instead, drug combinations, for example in pouches or bottles, which in turn can be placed in pouches, are arranged in storage vessels, which in turn are stored in the storage locations. The aforementioned unloading device serves to transfer the drug combinations arranged in the storage vessels to a transport device.

For the delivery of the drug combinations to a user, the picking device may include at least one delivery station coupled to the control device, in each case having a removal location and a user interface for communication with a user. The drug combinations may be transferred from the unloading device to the transport device, and the transport device connects the storage device to each delivery station in such a manner that that drug combinations may be conveyed to each delivery station.

The picking device may include a central storage device in which a reliable and mature technology is used. By combining the at least partially known storage device with an unloading device, a transport device, and at least one delivery station, it is possible to provide, based on known and proven storage technology, a picking device which is suitable for dispensing drug combinations compiled individually for each patient, and which is also kept constructively simple, requires little maintenance, and can dispense a plurality of drug combinations per unit of time.

Because the at least one delivery station includes a user interface, the picking device may dispense the drug combinations, customized to individual patients, to different types of users. By way of example, the drug combinations may be delivered to a "qualified user," which in the context of the present disclosure means a user who is permitted to dispense medicinal products to patients in accordance with the regulations of the country in which the device is used.

At a different delivery station, the patient himself/herself, hereinafter referred to as a "simple user," may initiate the dispensing of a drug combination. The aforementioned users may authenticate themselves through the user interface, wherein the necessary steps for the authentication may depend on the type of user.

For the case of a simple user, it may be necessary for the user to be identified via the user interface (e.g., by presenting an identity card) and to pay for the delivered drug combination (e.g., by inserting a credit card). Whereas, for a qualified user it may be sufficient that the user identifies himself/herself via a personnel number stored in the control device, wherein the payment process for the drug combination can be performed at another location (e.g., in a pharmacy). With the picking device, it is also possible to combine different types of delivery. One or more embodiments may include, for example, two delivery stations, wherein one is operated by a qualified user, while the other can be used by a simple user (e.g., the patient).

In contrast to some picking devices, in the picking device according to the disclosure, only drug combinations, and no drug packs, are stored in storage vessels in the storage device. Here, to remove the drug combinations from these storage vessels, the picking device may include an unloading device that transfers the drug combinations from the storage vessels to the transport device.

Typically, rectangular drug packs are stored in the known picking devices. So as to be able to accommodate the known and proven technology at least partially, the storage vessels of the picking device according to the invention are also preferably rectangular in form, at least in the operating device gripping area. That is, the stocking and retrieval of storage vessels may be performed similarly to the known stocking and retrieval of drug packs. Thus, a comprehensive adaptation of the storage device with respect to the storage itself is not required.

Depending on the drug combinations to be stocked, storage vessels of different sizes may be used. If storage vessels of different sizes are used, it may be necessary to report to the picking device which vessel size is used for a drug combination. This information may be necessary for the correct choice of the storage site and storage location, and for the ability to accordingly control the operating device.

To provide this information, the operating personnel performing the stocking may input a special identifier for a storage vessel being used for each drug combination, wherein exact dimensions of the storage vessel being used may be assigned to these identifiers. It is also possible to specify the type and/or size of the storage vessel as part of an identifier (e.g., a bar code) on the drug combinations. Furthermore (or additionally), it is possible to measure the storage vessel during the stocking operation, although this may be relatively complicated depending on the exact design of the storage vessels.

To ensure a smooth and rapid transfer of the storage vessels to the unloading device, in one or more embodiments the unloading device may include a vessel receptacle designed to correspond to a storage location and/or adaptable to the same, such that storage vessels may be transferred to the vessel receptacle by "conventional stocking movements" of the operating device. The term, "conventional stocking movements" in this context is used to mean those which the operating device executes to move storage vessels from and to storage locations, and from the stocking device. In one or more embodiments, no structural adaptation of the operating device may be necessary for the transfer of storage vessels to the unloading device, such that it is possible to rely on known operating devices. This in turn further reduces the maintenance requirements for the picking device as a whole.

In one or more embodiments, the drug combination(s) arranged in a storage vessel may be transferred from the unloading device to the transport device. For this purpose, the unloading device may have, for example, a gripper which removes the drug combinations from the storage vessel and transfers them to the transport device.

However, the use of a gripper is structurally complex and in turn increases the maintenance burden. In one or more embodiments, therefore, the unloading station may be a gravity unloading station of which drug combinations arranged in storage vessels may be transferred to the transport device at a receiving location via a discharge opening of a storage vessel. The term "gravity unloading station" is used to mean any unloading station where the drug combinations move out of the storage vessel via a discharge opening of the storage vessels by means of gravity.

This can be achieved, for example, by the storage vessel in the unloading station being rotated 180° in such a manner that a discharge opening which points upwards when in the storage state points downward, and the drug combinations fall out of the storage vessel. The storage vessel may also have a releasable base region which is temporarily opened for transferring the drug combinations to the transport device. In order to avoid slippage of clamping jaws against piece goods as they are retrieved, in one or more embodiments at least one section of the clamping surfaces of the clamping jaws includes a non-slip material. For example, either the jaw is made of such a non-slip material or the jaw is coated, at least in sections, with a non-slip material.

Occasionally, the drug combinations in the storage vessel may be slightly wedged. In order to facilitate gravity-induced unloading in such a case, in one or more embodiments the unloading device may be designed as a tipping station which may tip drug combinations arranged in storage vessels at a receiving location onto the transport device. During the unloading of the storage vessels, the tipping movement may be halted suddenly by a stop and the kinetic energy of the drug combinations may overcome the wedging. Occasionally, it may also happen that the tipping movement is not sufficient to remove drug combinations from a storage vessel. In order to (further) facilitate the removal of the drug combinations from storage vessels, whether in cases where there is a tipping station or where there is an unloading station with a different design, in one or more embodiments the unloading station may include an ejection device which ejects drug combinations arranged in storage vessels via the discharge opening of a storage vessel onto the transport device.

The ejection device may be designed in such a way that the drug combinations are ejected by an ejector that is moved through an opening in a storage vessel. In one or more embodiments, the ejection device may have a compressed air nozzle, and the drug combinations may be moved out of the storage vessels by compressed air.

Typically, the storage device of the picking device may be rectangular in form, with two parallel rows of shelves forming an alley between them in which the operating device may be moved horizontally and vertically. In order to avoid the need to guide the transport device into the storage device, which would, inter alia, result in a reduction in the storage capacity of the storage device, in one or more embodiments the unloading device may have a movable vessel receptacle that collects storage vessels which will be emptied, and which are in a park position, and moves the same to an emptying position. In an unloading device designed accordingly, it is possible, for example, that the transport device is constructed at least partially as a horizontal conveyor belt parallel to one of the sides of the storage device. In the park position, which is comparable to a storage location, a storage vessel may be collected by the movable vessel receptacle and/or transferred by the operating device to the vessel receptacle, and then moves with the movable vessel receptacle into an emptying position where drug combinations arranged in storage vessels are transferred to the transport device (e.g., by the storage vessel being tipped).

If a movable vessel receptacle is used, moreover, the vessel receptacle may have a retaining device through which storage vessels may be held in a temporary manner allowing later detachment. Such a retaining device prevents the storage vessel from slipping during transport and the emptying can be carried out more easily.

After the storage vessels are emptied, they may be collected again by the operating device and returned to a free storage location of the storage device. However, this approach wastes valuable storage space. As such, in one or more embodiments of the picking device, the unloading device may be associated with a vessel collection device that collects storage vessels emptied at the unloading device. Storage of empty storage vessels in storage locations of the storage device is thus avoided and more storage vessels containing drug combinations may be held in the storage device. The vessel collection device may be constructed outside of the storage device.

The manner in which the emptied storage vessels are transferred from the unloading device to the vessel collection device depends on their arrangement inside the picking device. To make it possible to perform the transfer of the emptied collection vessels from the unloading device to the vessel collection device particularly rapidly, the vessel collection device may be arranged below a section of the unloading device in such a manner that emptied storage vessels may be conveyed to the vessel collection device by releasing the retaining device. Once the storage tank has been emptied (e.g., by tipping), the retaining device may be released at a designated transfer location and the storage vessel may be conveyed by gravity to the vessel collection device. For this purpose, the vessel collection device may be constructed, by way of example, vertically, and arranged directly below a base opening of the unloading device with a corresponding design. In a corresponding embodiment, the unloading device may have a section that is arranged outside of the storage device, wherein a receiving section of the vessel collection device for storage vessels may be arranged below that section.

In order to allow the user to easily remove the emptied storage vessels from the vessel collection device, the vessel collection device may have an access opening accessible from outside the storage device.

The picking device may have at least one delivery station via which the drug combinations may be delivered to a user. For this purpose, a storage vessel which contains the drug combination to be retrieved may be emptied at the unloading device, and the drug combination may be transported by the transport device to a delivery station and transferred to the user. To enable a particularly rapid dispensing of a drug combination, the picking device may have in the storage device and in addition to the at least one delivery station, a discharge device which is arranged at least partially within the radius of action of the operating device, and which is accessible from outside the storage device. By way of example, a qualified user, such as a pharmacist, may request a retrieval of a storage vessel, with its drug combination, via a corresponding delivery device in order to pass the drug combination to a waiting customer. For this purpose, a storage vessel containing a drug combination to be retrieved may be transferred to a section of the delivery device when the same is positioned in the radius of action of the operating device, and may be conveyed to an access area of the user. Such a delivery device may, for example, be designed as a simple slide.

As set forth above, the picking device may include a vessel collection device for receiving emptied storage vessels. Alternatively or additionally, the picking device may have a vessel provision device, accessible from outside the storage device, for emptied storage vessels. For example, this vessel provision device may be a type of slide on which storage vessels emptied by the operating device are placed, and which are then conveyed to a removal location of the vessel provision device. In a corresponding picking device, the emptied storage vessels may thus be furnished for reuse immediately after emptying, thereby reducing the number of the storage vessels in circulation. A section of the vessel provision device may be arranged in such a manner that empty storage vessels may be fed directly to this section by the unloading device.

The picking device may have at least one delivery station with a removal location as well as a user interface. In order for a drug to be dispensed via the delivery station, user authentication may be required. The manner of authentication in this case, as described above, depends on whether the user is a qualified user or a simple user. Here, the picking device may be operated both by a qualified user and by a simple user. For this purpose, the picking device may have at least two delivery stations that are suitable for different types of access of different users. The two delivery stations may be identical in design, with only different authentication procedures being required. In the case of a qualified user, for example, it may be sufficient for the user to authenticate only once within a predetermined time interval.

However, the two delivery stations may also be adapted to the type of user, such that one delivery station may be operated by a qualified user only, whereas the second delivery station may be configured such that a simple user can operate it as well. Which user can operate a delivery station may be determined by a special configuration and/or design of the user interface.

In known picking devices, the delivery of drugs, whether in the form of drug combinations or drug packs, is only possible if a user can enter the premises where the picking device is housed. However, such a restriction of the possibility of removal of medicinal products does not satisfy the access criteria of a modern user. In one or more embodiments of the picking device, the picking device therefore may include a delivery station that is operable from outside a building in which the storage device is arranged. A corresponding delivery station may then, for example, be designed as a so-called "drive-through station" in which a user pulls up with a motor vehicle, identifies himself/herself at the delivery station, and after successful completion of the full authentication procedure, receives a drug combination. If a transfer of medicinal products in a certain country requires personal contact with a qualified user (e.g., a pharmacist), an accordingly designed delivery station may also have communication systems via which the qualified user may inform the simple user, who is picking up the drugs, of the risks and side effects of the drugs, by way of example.

As set forth above, the picking device may include a vessel provision device for empty storage vessels. In the case of storage devices with high storage capacity, it happens regularly that drug combinations are not retrieved within a certain time period because they are not picked up by a user for whom they were compiled. Thus, the picking device may therefore have a vessel delivery device for storage vessels with overdue drug combinations. An operator of the picking device may freely determine when a drug combination is to be considered "overdue." For example, if a four-week period is specified, the picking device may automatically transfer all drug combinations that have been stored in the storage device for more than four weeks, along with the storage vessels, to the vessel delivery device for overdue drug combinations.

The picking device may have a first identification device by which drug combinations are identified prior to stocking. This first identifying device may be functionally assigned to the stocking device, and automatically identify all of the drug combinations transferred to the stocking device, specifically by an identifier assigned to the drug combination. An identifier may be, for example, a barcode. The information which an identifier includes depends, inter alia, on country-specific requirements, the merchandise management system, etc.

In one or more embodiments of the picking device, a second identification device may be included by which drug combinations may be identified prior to the emptying of the storage vessels in the unloading device. The provision of the second identifier increases security as regards the dispensed drug combinations. For the stocking of a drug combination, the same is assigned an empty storage location by the control device. This means that a link is established between a storage location and a drug combination, such that the control device knows at all times which drug combination is arranged at which storage location. The nature of the drug combination is normally not relevant for the selection of the storage location as a drug combination and/or the corresponding storage vessel is stored inside the storage device where there is space. The stocking of the storage vessels is thus carried out according to the principles of dynamic or chaotic storage. Optionally, certain storage locations may be preferred due to their proximity to the unloading device. If the storage device includes a special storage location for drug combinations which must be cooled, this may be taken into account during the stocking.

In exceptional cases, there may be a malfunction of the storage device, when an operator is forced to enter the storage device to correct the malfunction. It may happen in such cases that the operator moves one or multiple storage vessels, such that they are moved to the "wrong" storage location. A "wrong" storage location in this case is one which the control device has not linked to a drug combination. In such a case, a storage location A where the control device expects to find a drug combination X1 may come to contain a drug combination X2 as a result of the intervention of the operating personnel. When the drug combination X1 is requested from storage location A, the drug combination X2 would then be retrieved. Here, there may be another identification prior to the emptying, such that it is possible to compare whether the drug combination which should be situated in the storage location is actually in the storage location. Although the error rate of the storage device described here is extremely low, such a verification may be particularly useful when highly sensitive drug combinations are stored.

A method for retrieving drug combinations arranged in a picking device in storage vessels is also provided.

A drug combination to be retrieved may be identified by a user providing uniquely identifying identification data for a drug combination to be retrieved, and by the storage location inside the picking device being determined.

The nature of the identification data may depend on the precise process control, country-specific requirements, and optionally the merchandise management system which is used to operate the picking device. By way of example, if a simple user uses the picking device to retrieve a drug combination, the characteristics may include, among other things, the name of the user and/or a personal number uniquely identifying him/her (e.g., a social security number). An identification document may also be scanned to furnish the identification data. In addition to personal data, the identification data may also include precise information about the drug combination as such (e.g., a unique index number or the like). A prescription or the like may also be read in to furnish the identification data, or that data may be read in from a customer card, or a pin code may be requested, or a bar code may be scanned, for example.

After the drug combination is identified, an operating device may be moved to a storage location assigned to the drug to be retrieved by the operating device, and a storage vessel arranged at the storage location and containing the drug combination, may be gripped and transferred to a vessel receptacle of an unloading device. The storage vessel transferred to the vessel receptacle may be emptied onto the transport device and the drug combination may be transported by the transport device to a removal location of a delivery station. The removal location may also be cleared for the removal of the drug combination upon instructions from a control device coupled to the delivery station.

Which steps a user needs to perform in order for the control device to provide instructions to release the drug combination depends on whether a qualified or simple user is operating the delivery station. The relevant details are set forth below.

As stated above, the function and construction of the storage device of the picking device is partially known. In order to preserve the conventional functionality upon the transfer of a storage vessel to the unloading device, in one or more embodiments the vessel receptacle may be arranged prior to the transfer of the storage vessel in such a manner that the operating device may transfer the storage vessels using "conventional" stocking movements (see above). In this way, the transfer of a storage vessel to the vessel receptacle may be performed analogously to a stocking operation of a storage vessel in a storage location. Additional, and thus time-consuming, movement sequences of the control unit are not necessary. Likewise, a structural adjustment is also unnecessary.

The storage vessel may be emptied by the vessel receptacle being tipped, such that drug combinations fall onto the transport device. A corresponding tipping process may be triggered in a particularly simple manner, without the need to include complicated mechanical devices in the unloading device or on the storage vessel itself.

In order to avoid the need to move the transport device into the storage device to receive the drug combinations, the vessel receptacle may be moved prior to the emptying of the storage vessel from a park position into an emptying position. In the park position, the vessel receptacle may collect a storage vessel to be emptied. The park position is therefore comparable to a storage location. In the emptying position, the storage vessel may be emptied onto the transport device (e.g., by tipping). This emptying position may be selected such that the transport device may be guided parallel to an outer wall of the storage location, by way of example.

After the storage vessel is emptied, it must be removed from the unloading device. By way of example, it may be temporarily stored in a free storage location of the storage device by the operating device. However, this would waste precious storage location. Therefore, in one or more embodiments, a storage vessel may be transferred into a vessel collection device or a vessel provision device after the emptying. In the vessel collection device, emptied storage vessels are temporarily stored until they are removed by an operator from the vessel collection device. In contrast, the emptied storage vessels may be continuously provided to the operator by the vessel provision device, because the vessel provision device may be configured in such a manner that a section of the same may be accessed from outside of the storage device. The manner in which the emptied storage vessels are moved into and/or to the vessel collection device or the vessel provision device depends on the arrangement of these relative to the unloading device. If the vessel collection device, or at least a section of the vessel provision device, is arranged below the unloading device, the emptied storage vessels may be transferred by gravity through a base opening of the unloading device. The same applies to the vessel provision device.

As stated above, the retrieval process begins when a drug combination to be retrieved is identified. The manner in which this identification is carried out can also, as indicated above, depend on the type of the user of a delivery station. Thus, a drug combination to be retrieved may be identified by personal data of a user being provided as the identification data and evaluated. On the basis of the personal data, a drug combination assigned to a user for retrieval may then be determined by the control device.

If a user is assigned several drug combinations, the user may be given the opportunity to select the drug combinations to be delivered. This can be done, for example, by the user interface displaying on a display device the plurality of drug combinations available for the user, and the user selecting the drug combinations which should be dispensed. The non-dispensed drug combinations then remain in the picking device. By way of example, it may happen that only a portion of the drug combinations is dispensed, either for cost reasons or because a user is assigned drug combinations for a family member who is a minor and who is not present for a longer period of time. Here, storage in a storage device specially designated for such a case may be more appropriate.

Once a drug combination to be retrieved has been identified, the dispensing process commences. Over the course of this dispensing process, the drug combination is transported to a removal location of a delivery station. If the user is a simple user, this simple user generally is required to pay for the drug combination or drug combinations. The drug combinations are therefore only released by the control device once the payment process has been successfully completed. However, it may happen that the user is not willing, or simply is not able, to make a payment. Since, however, the drug combination assigned to the user is already in the removal location, it is necessary in such a case that it be removed from the removal location. For this purpose, the delivery station may have special components by which it is possible to remove drug combinations from the removal location that have not been removed.

However, the steps of the retrieval method following drug retrieval may only be carried out if all user actions associated with the retrieval have been performed successfully. The user actions mentioned above can be country-specific, or can be pre-specified by the drug combination being retrieved, by way of example. For example, it may happen that drug combinations require payment, or are free of charge, depending on the included drug combination. In addition, an image capture of the user may be required prior to the dispensing of a drug combination, or the user may be required to leave an electronic signature, wherein the user interface may furnish special processes for all national requirements. With the method detailed above, it is possible to prevent commencement of the retrieval of a drug combination before all the necessary user actions have been performed successfully.

As already explained above, it may happen (e.g., in the case of a malfunction of the storage device) that storage vessels are displaced by operating personnel. In order to prevent the dispensing of potentially incorrect drug combinations, a drug combination arranged in a storage vessel may be identified with a second identifier prior to the emptying of the storage vessel, and the storage vessel may only be emptied if the identified drug combination corresponds to the drug combination identified with the identification data.

If the identified drug combination does not correspond to the drug combination identified by the identification data, the same may be removed from the stock of the storage device. This stock removal may be accomplished, for example, by the storage vessel being conveyed to a vessel return device, which typically serves to remove expired drug combinations from stock. The drug combination may also be moved not onto the transport device, but rather onto a special return device via which the drug combination is removed from the stock of the picking device and/or the storage device.

FIG. 1 is a schematic plan view of one or more embodiments of a picking device. The picking device 1 includes a central storage device 2 with two opposite rows of shelves 10, between which an alley 15 is formed, in which an operating device 20 coupled to a control unit (not shown) is arranged in a manner allowing movement horizontally and vertically. The operating device 20 includes a gripper 21 that can rotate about a vertical axis of rotation, such that the two opposite rows of shelves 10 may be served with one gripper 21. With the gripper 21, storage vessels 3 are moved to storage locations and removed from the same when a drug combination arranged in a storage vessel 3 is being dispensed. Any embodiment known to a person skilled in the art, with which rectangular bulk goods can be stocked and retrieved, can be considered as a gripper 21. In the illustrated embodiment, a jaw gripper with jaws 27, a contact surface 28 for storage vessels 3, and a sliding mechanism (e.g., pushing device) 29 is used. For the retrieval function, storage vessels 3 are grasped by the jaws 27 and drawn onto the contact surface 28. For the movement of storage vessels 3 to storage locations or to the vessel receptacle (see the following figures), a storage vessel 3 is accordingly pushed by the pushing device 29.

Each row of shelves 10 includes multiple shelves 11 (see FIGS. 3 and 4) extending in a plane, with multiple storage locations 5 for storage vessels 3, 3', 3". The storage locations 5 are not physically separated from one another on the shelves 11. As such, there are—so to speak—"virtual" storage locations. As can be seen in FIG. 1, storage vessels 3, 3', 3" of different sizes can be stored on the rows of shelves 10. The storage devices 2 which are used can be specified to the control device 100 (see FIG. 5), for example, when the drug combination is identified. This may also be determined by the operating device 20, by way of example, when the storage vessel 3, 3', 3" is removed from the stocking device (see the following figures). Finally, special sensors can be included which determine the size of the storage vessel 3, 3', 3". As long as storage vessels 3, 3', 3" of only one size are used, the above measures are unnecessary.

In an one or more embodiments, the storage locations may be formed on L-shaped struts attached to rear walls, for example, wherein the storage vessels are then usually stored between and/or on two struts. In such a case, it may be necessary to position the struts according to the size of the storage vessels, such that if differently sized storage vessels are used, differently designed storage areas are necessary. However, in terms of the stocking or retrieval of the storage vessels, there are no further differences.

Drug combinations 4, 4', 4" are arranged in the storage vessels 3, 3', 3". A drug combination is a combination of at least one drug portion, wherein a drug combination also includes multiple drug portions of several different types of drugs which are then arranged, for example, in multiple vials which in turn are arranged, for example, in a pouch on which an identifier is then affixed. Thus, the drug combination can be uniquely identified. Regardless of the form and the packaging of the drug combination, it is important that it includes an identifier, wherein the control device can identify each drug combination using the identifier. Several drug combinations may also be arranged in one storage vessel. A drug combination may be assigned to a user based on personal identity, as set forth in detail further below in the description of the method.

The picking device shown in FIG. 1 further includes a transport device 50 with a first transporter 51 and two second transporters 52. The first transporter 51 may be a conveyor belt, by way of example, which is arranged in the illustrated embodiment parallel to the lower row of shelves, outside the housing of the storage device. On each of its ends, the first transporter 51 transitions into a second transporter 52, which may likewise be designed as a conveyor belt, and which may be in turn coupled to a delivery station 80. Due to the interaction of the first transporter 51 with the two second transporters 52, the first transporter 51 may be moved in two directions, as is indicated by the arrow.

Each delivery station 80 includes a removal location 81 as well as a user interface 82, which will be described in detail with reference to subsequent figures.

The storage device 2 may be coupled via an unloading device 60 to the transport device 50 in such a manner that drug combinations may be transferred by the unloading device 60 from the storage vessels 3, 3', 3" to the transport device 50. This is described in greater detail below with reference to subsequent figures.

Figure 2:
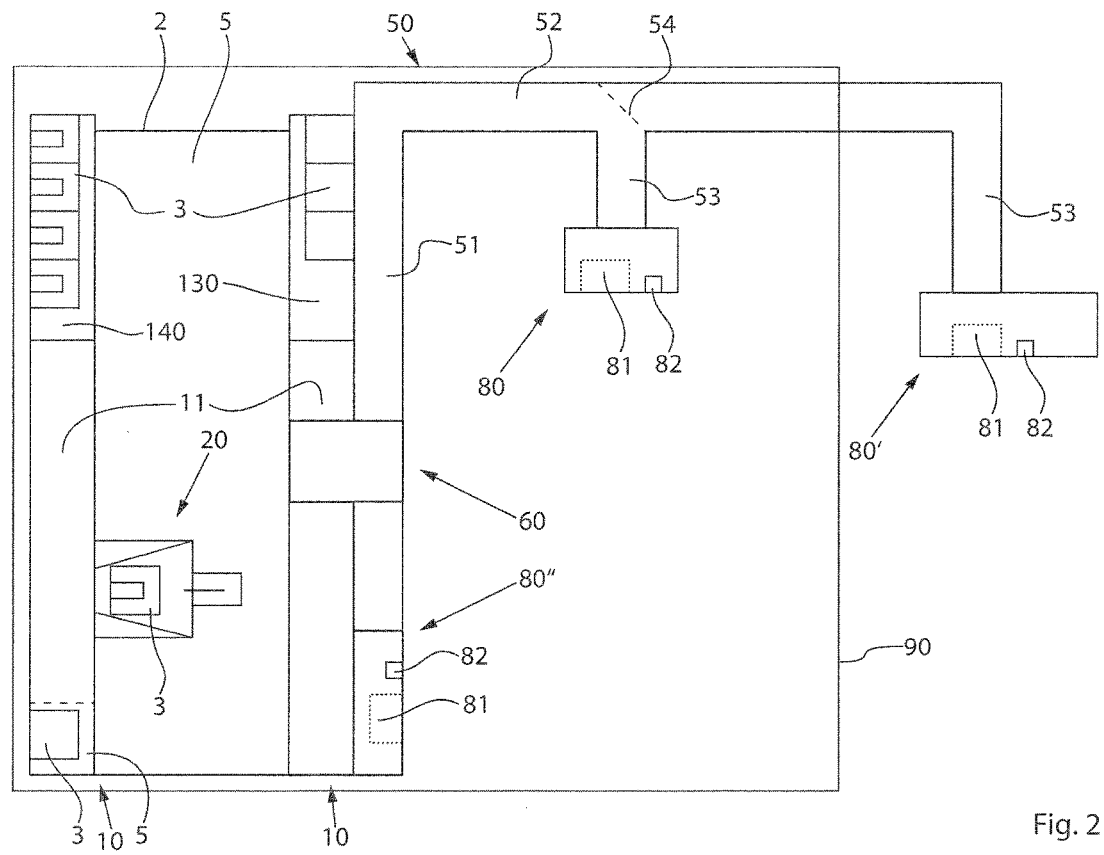
FIG. 2 is a top view of one or more embodiments of a picking device.

In one or more embodiments as shown in FIG. 2, the storage device 2 may include, in addition to the elements described above, a vessel provision device 130 which is constructed inside a row of shelves 10, wherein emptied storage vessels 3, 3', 3" may be transferred to the same. The vessel provision device 130 may convey the emptied storage vessels 3, 3', 3" in such a manner that they may be removed from outside the storage device 2. By way of example, the vessel provision device 130 may be designed as a kind of slide, such that emptied storage vessels 3, 3', 3" set down by the operating device 20 may be conveyed by gravity to a removal location 81 that is accessible from outside the storage device 2.

Moreover, the picking device 1 may include a vessel return device 140 for drug combinations 4, 4', 4" which were not requested within a predetermined time frame. The vessel return device 140 may be designed to correspond to the vessel provision device 130, with the difference that storage vessels 3, 3', 3" still filled with drug combinations 4, 4', 4" are returned via the vessel return device 140.

The picking device 1, according to one or more embodiments, may have three delivery stations 80, 80', 80", wherein the delivery stations 80, 80" may arranged inside a schematically-indicated building 90. The delivery station 80' may be arranged outside the building 90, or at least is accessible from outside of the building 90, and may be designed as a "drive-through station", by way of example. The three delivery stations 80, 80', 80" are coupled to the storage device 2 via the transport device 50 in such a manner that drug combinations can be supplied from the storage device to each of the delivery stations 80, 80', 80". Here, the delivery station 80" may be directly connected to the first transporter 51 constructed parallel to the storage device 2, whereas the delivery stations 80, 80' may be connected by second and third transporters 52, 53. To selectively convey drug combinations 4, 4', 4" to the delivery station 80 on the second transporter 52, a directing element 54 may be functionally assigned to the second transporter 52, and may be moved into the path of movement of the transporter 52, thereby conveying the drug combinations 4, 4', 4" onto the third transporter 53 assigned to the delivery station 80. The transporters 51, 52, 53 may be designed as simple conveyor belts, by way of example, wherein the transporter 51, as already indicated in FIG. 1, may be moved in two directions to be able to reach the stations 80, 80', 80".

Figure 3:
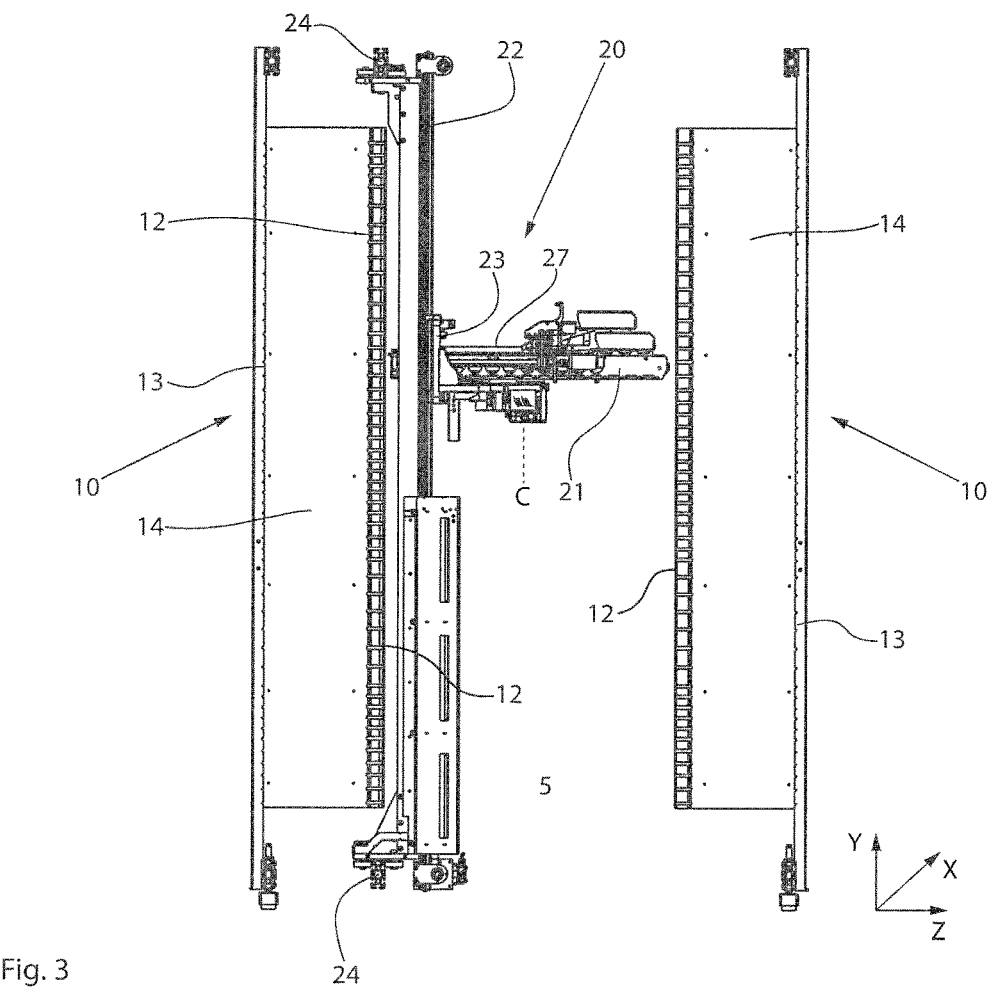
FIG. 3 is a front view of the interior of a storage device.

FIG. 3 shows a front view of the interior of the storage device 2, with two opposite rows of shelves 10, with multiple superimposed shelves 11 each extending in a plane, and arranged behind dividers 14. FIG. 3 particularly shows the design and arrangement of the operating device 20 inside an alley (e.g., lane) 15 between the opposite rows of shelves 10. The operating device 20 may include a gripper 21, which may be moved on a vertical guide 22 by a drive 23. The vertical guide 22 may be moved on horizontal guides 24 by a drive 25, such that the operating device 20 and the gripper 21 may be moved horizontally and vertically within the alley 15 on the vertical and horizontal guides 22, 24. The gripper 21 may rotate about a vertical axis of rotation, indicated by C. As can be seen in FIG. 3, front loading edges 12 of the rows of shelves 10 and/or the shelves 11, facing the alley 15, may be constructed in parallel, perpendicular to each other, such that it is not necessary, given a corresponding design of the operating device 20, to move the same in the Z-direction. All storage locations 5 on the shelves 11 may be reached without a movement of the gripper 21 in the Z-direction. The depth of the storage locations 5 is defined via the distance of the front edge 12 of the shelves 11 and/or the rows of shelves 10 from the rear wall 13. Provided that the distance between the front edge 12 and rear wall 13 permits, two storage vessels 3, 3', 3" may be stored one behind the other, as long as the potential need to execute a swap of stock is taken into account in cases where only the rear storage vessel 3, 3', 3" will be retrieved.

Figure 4:
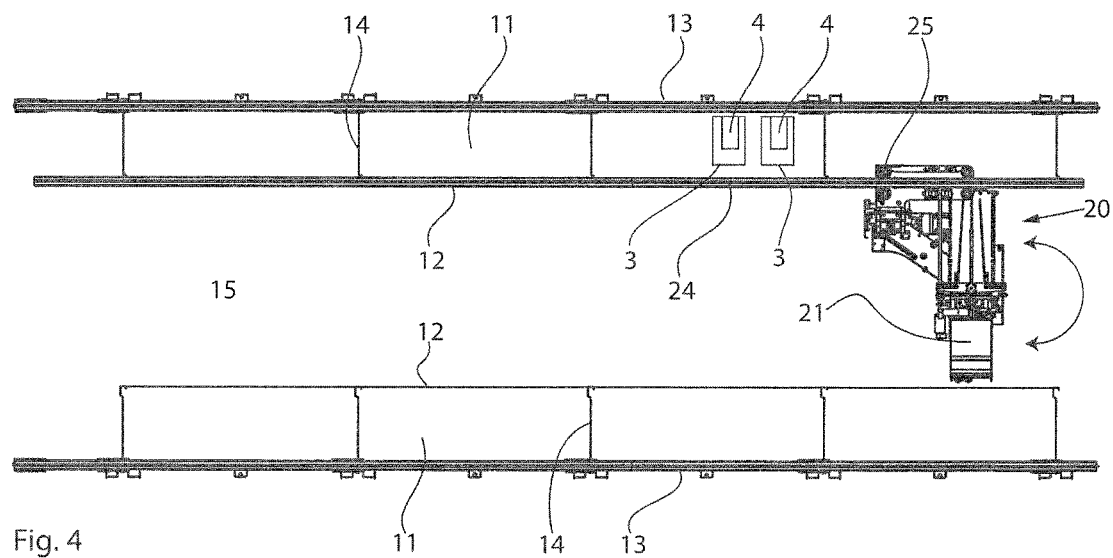
FIG. 4 is a top plan view of the storage device of FIG. 3.

FIG. 4 shows a plan view of the storage device 2, wherein the operating device 20 can be seen in the alley 15. In the top view according to FIG. 5, one shelf 11 is visible for each of the rows of shelves 10, with each shelf 11 separated by multiple dividers 14. Two storage vessels 3, 3', 3" may be arranged on the upper shelf 11, each with one drug combination 4, 4', 4". As FIG. 4 shows particularly clearly, the end face of the gripper 21 may be aligned with the front edge 12 of the shelf 11, that is, between the shelf 11 and the contact surface 28 of the gripper 21, only a very small gap exists. If the gripper 21 rotates around the C-axis as arranged in FIG. 3, the storage locations 5 of the "lower" row of shelves 10 can be served accordingly.

Figure 5:
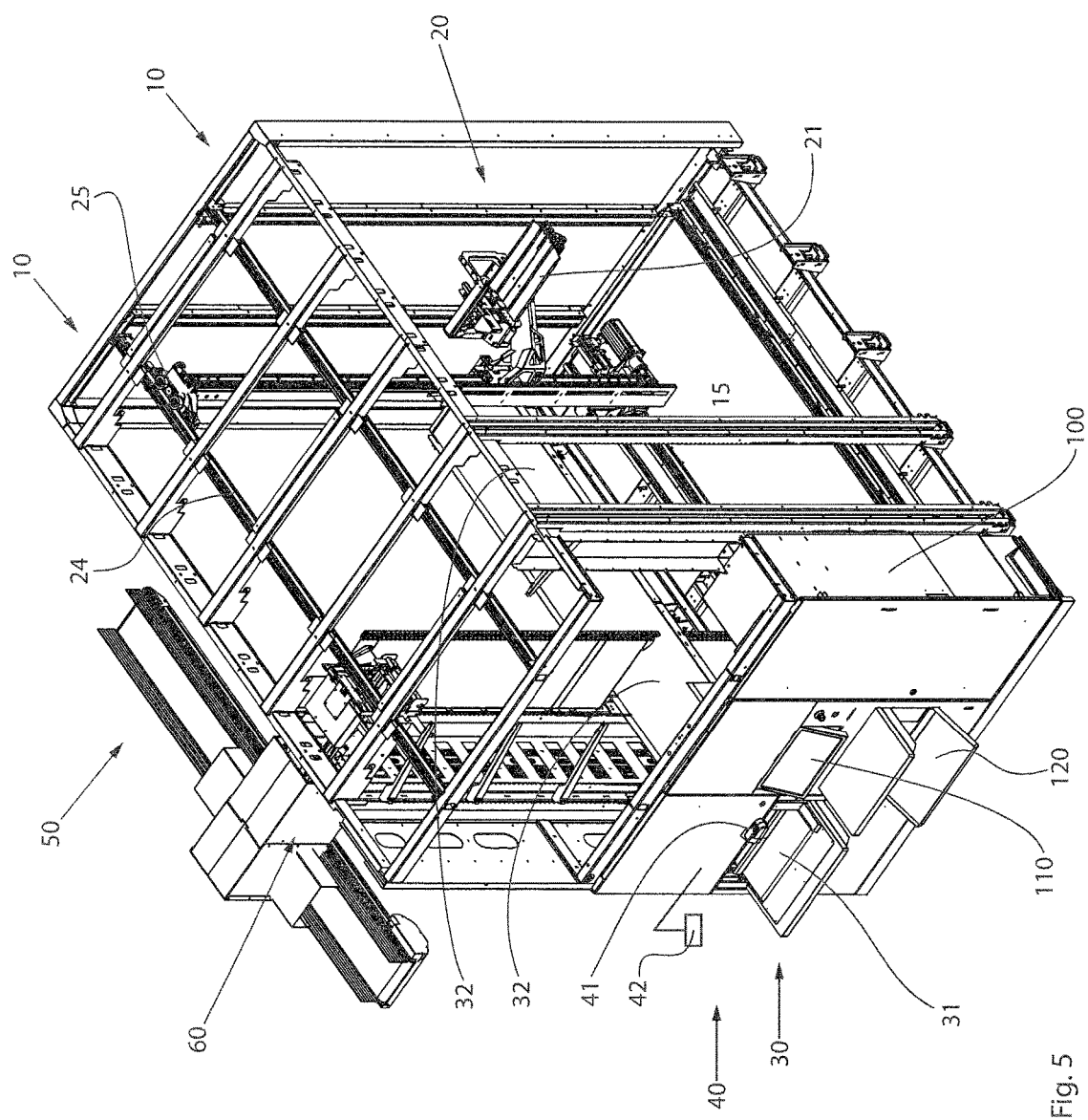
FIG. 5 is a perspective view of storage device in combination with an unloading device and a transport device.

FIG. 5 shows a schematic illustration of a combination storage device 2 and transport device 50. In the illustration shown in FIG. 5, the storage device 2 is only partially shown, particularly so as to illustrate the components arranged within the storage device 2. The storage device 2 in turn may include two parallel rows of shelves 10, between which an alley 15 is formed. For clarity, the shelves 11 and the dividers 14 are not shown. These correspond to the components described with reference to FIGS. 3 and 4. FIG. 5 shows that the storage device 2 may include a stocking device 30 which partially protrudes from the storage device 2 on the front end face thereof. The stocking device 30 includes a stock section 31 on which storage vessels 3, 3', 3" filled with drug combinations 4, 4', 4" may be placed. Once the storage vessels 3, 3', 3" are placed on the stock section 31, they will be moved into the storage device 2 by a transport assembly 32, which extends into the storage device 2 and which is usually designed as a conveyor belt. The storage vessels 3, 3', 3" may then be removed by the operating device 20 and conveyed to a storage location 5.

A first identification device 40 may be functionally assigned to the stocking device 30 and may identify a drug combination 4, 4', 4" before transport into the storage device 2. For this purpose, the first identification device 40 may be a hand-held identification reader 42, by way of example, with which operating personnel identify the drug combination to be stocked. After the identification, the drug combination 4, 4', 4" is placed in a storage vessel 3, 3', 3" and moved into the storage device 2 by the transport assembly 32. Alternatively or additionally, the first identification device 40 may include a second identification reader 41, by which a drug combination 4, 4', 4" arranged in storage vessels 3, 3', 3" can be automatically identified.

The storage device 2, as shown in FIG. 5, may further include a control device 100 coupled to the stocking device 30, to the first identification device 40, and to the operating device 20, and performs the control of these as well as the entire stocking and retrieval process. It is not essential that the control device 100 be arranged inside the storage device 2. The control device 100 may also be arranged outside of the storage device 2 for maintenance purposes. The only essential feature is a coupling of the control device 100 to the aforementioned components.

A display 110 may be arranged on the end face of the storage device 2, wherein via the display 110 the operator can see information relating to the storage device 2 and/or drug combinations 4, 4', 4" to be stocked or retrieved. The display device 110 may also be designed such that it is simultaneously an input device (e.g., a touch screen). A delivery device 120 may also be arranged on the end face of the storage device 2, wherein drug combinations 4, 4', 4" may be delivered to a user.

In FIG. 5, the unloading device 60 is also arranged in the upper section of the "left" row of shelves 10, extending from inside the storage device 2 to the outside, specifically above a transporter of the transport device 50, wherein the transporter in the shown embodiment extends parallel to the storage device 2.

Figure 6:
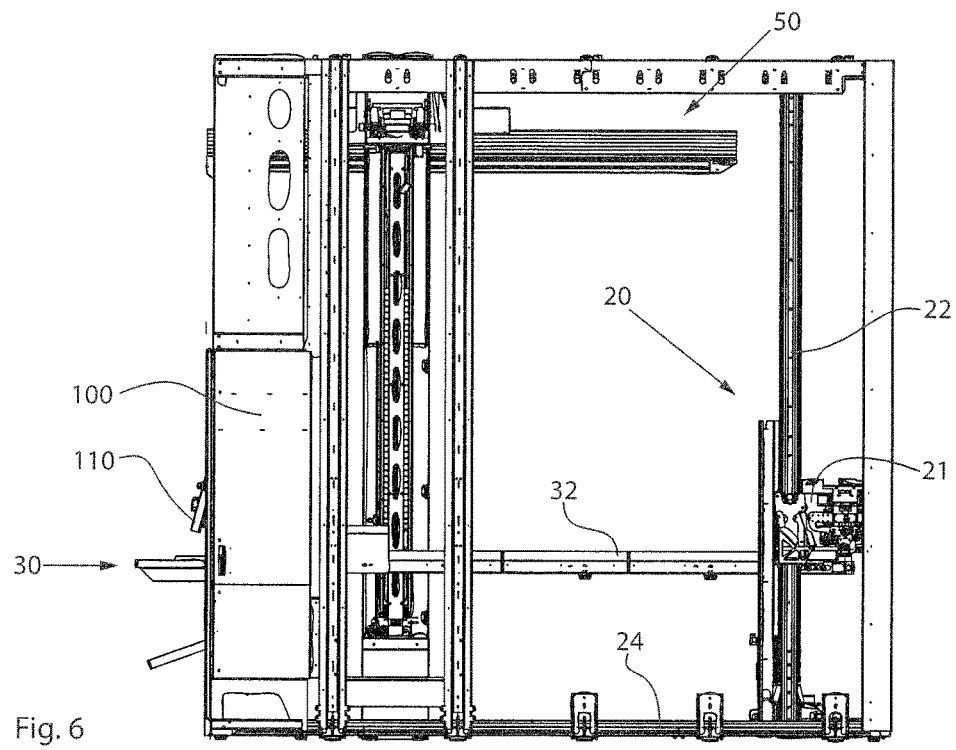
FIG. 6 is a side view of the storage device combination of FIG. 5.

FIG. 6 shows a side view of FIG. 5, wherein this figure particularly shows that the transport medium 32 of the stocking device 30 extends through the storage device 2. A corresponding design is not essential, but facilitates the removal of storage vessels 3, 3', 3", on the one hand, while simultaneously creating a temporary buffer for storage vessels 3, 3', 3" which have been identified and moved into the storage device 2, but have not yet been placed in a storage location 5.

Figure 7:
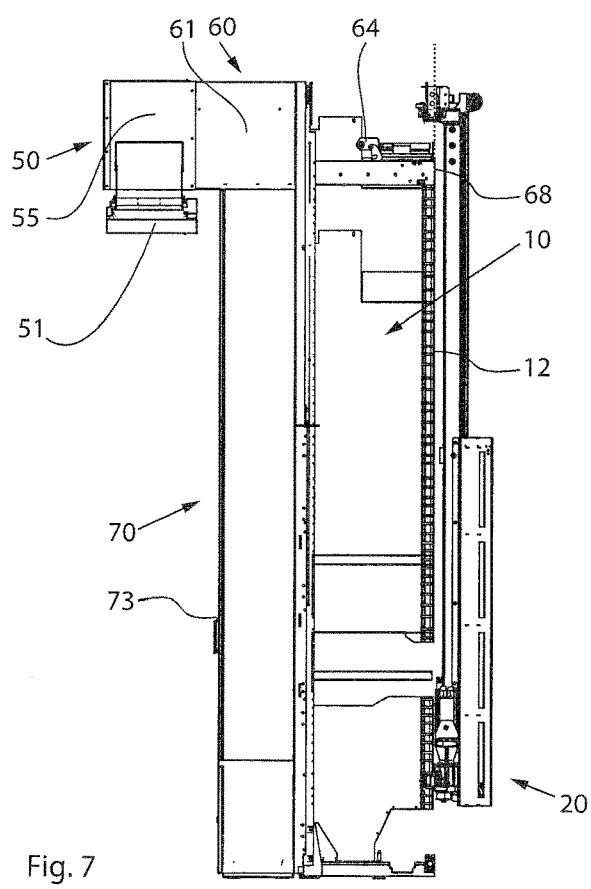
FIG. 7 is a front view of the storage device combination of FIG. 5.

FIG. 7 shows a front view of the "left" region in accordance with FIG. 5. In particular, FIG. 7 shows how the transport device 50 is arranged with respect to the storage device 2. Of the storage device 2, only the left row of shelves 10, the operating device 20, and the unloading device 60 are indicated.

As can be seen in FIG. 7, the unloading device 60 extends from inside the storage device 2 to the outside, namely in such a way that drug combinations 4, 4', 4" may be transferred to the first transporter 51 of the transport device 50, the first transporter 51 having a cover 55. As FIG. 7 further shows, the front edge 68 of the unloading station 60 sits flush with the front edge 12 of the row of shelves 10, such that the unloading device 60 may be loaded with storage vessels 3, 3', 3" by "conventional" loading and retrieval movements of the operating device 20. For this purpose, the unloading device 60 includes a vessel receptacle 64 which can be moved in inside the unloading device 60 towards the transport device 50, wherein the final position of this movement is hidden in FIG. 7 by the cladding 61 of the unloading device 60.

A vessel collection device 70 may be arranged below the outer section of the unloading device 60 and may have an access opening 73 through which emptied storage vessels 3, 3', 3" collected in the vessel collection device 70 may be removed. The vessel collection device 70 is described in more detail with reference to subsequent figures.

Figure 8:
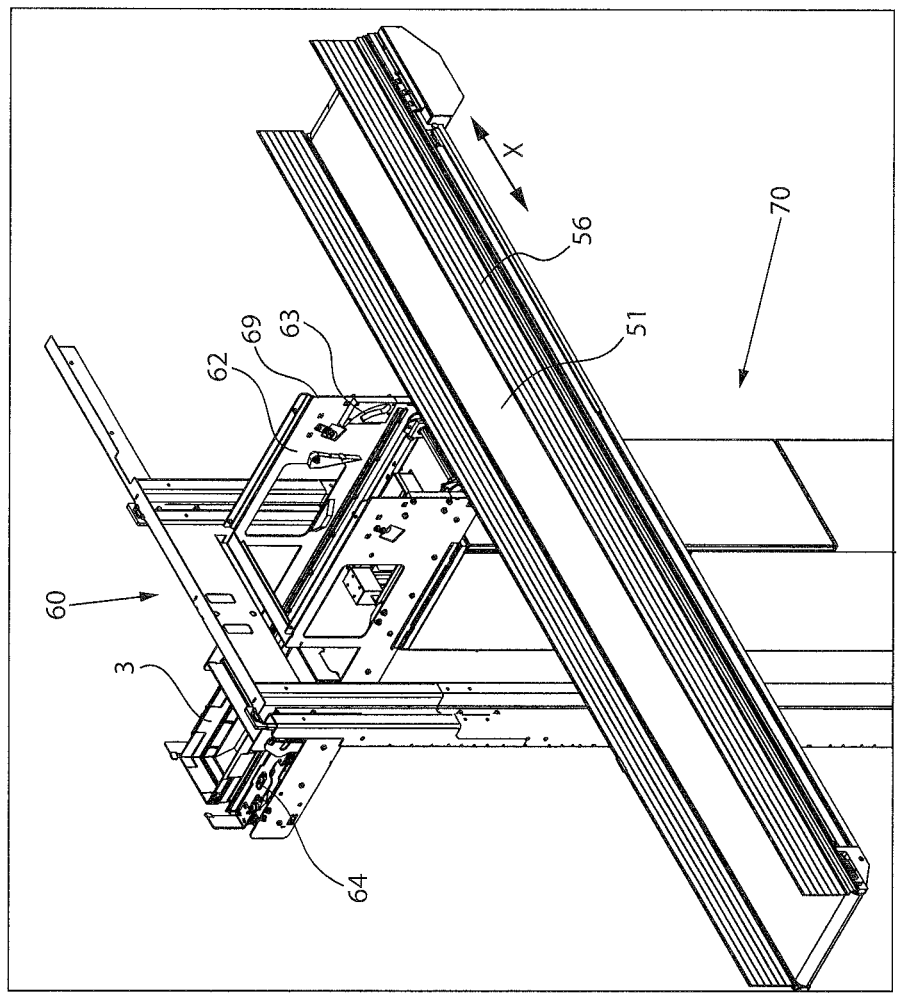
FIG. 8 is a perspective view of an unloading device/transport device transition region.

FIG. 8 shows a detailed view of a combination unloading device 60 and transport device 50, wherein a section of a vessel collection device 70 is indicated below the section of the unloading device 60 that is arranged outside the storage device 2. As shown in FIG. 8, the first transporter 51 of the transport device 50 is arranged perpendicular to a discharge end face 69 of a frame structure 62 of the unloading device 60, wherein tipping receptacles 63 for vessel receptacles 64 can be moved in the unloading device 60 are may be arranged in this discharge end face 69. The vessel receptacle 64 has two tipping projections (not shown in this figure) which cooperate to tip the storage vessel 3, 3', 3" at the front side of the unloading device 60 with the tipping receptacles 63. In order to prevent drug combinations 4, 4', 4" tipped from storage vessels 3, 3', 3" onto the transport device 50 from falling from the first transporter 51, the transport device 50 and/or the first transporter have lateral guides 56.

Figure 9:
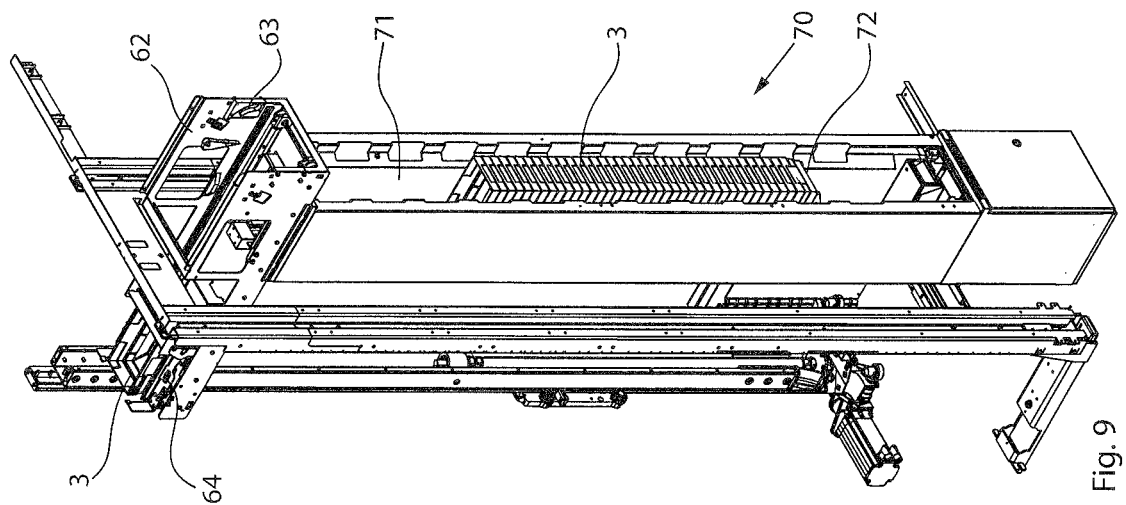
FIG. 9 is a perspective view of a combination unloading device/vessel collection device.

FIG. 9 shows the vessel collection device 70 arranged below the section of the unloading device 60 that is arranged outside of the storage device 2 in greater detail. This includes a vertical, elongated receiving space 71 in which multiple storage vessels 3, 3', 3" are arranged on a vertically-movable vessel support 72. Here, the emptied storage vessels 3, 3', 3" are transferred through an opening in the bottom of the frame structure 62 to the vessel collection device 70, wherein the transfer process is described in more detail in a subsequent figure.

Figure 10A:
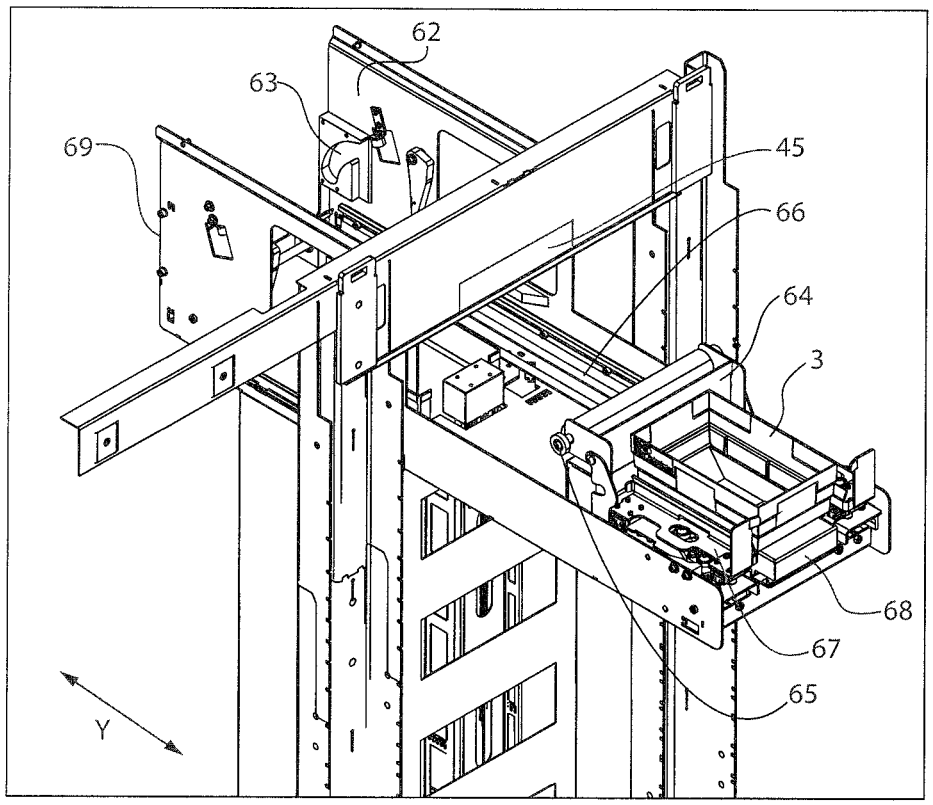
FIGS. 10*a* and 10*b* are perspective partial views of the unloading device of FIG. 9.
Figure 10B:
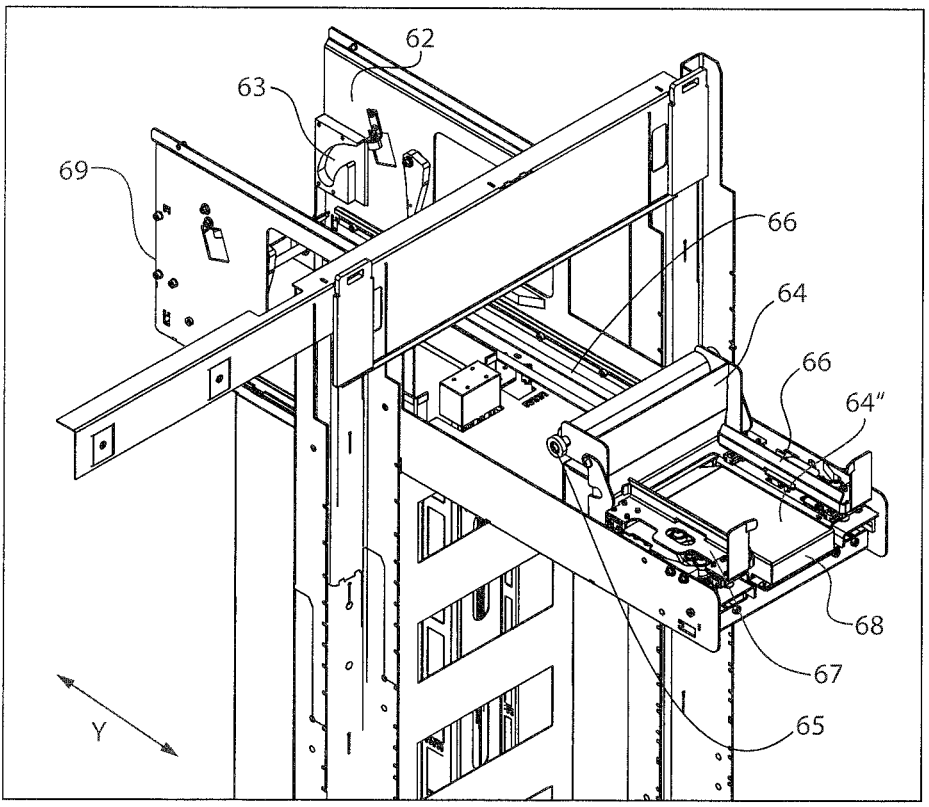

FIGS. 10*a* and 10*b* show detailed views of the unloading device 60. The two figures differ in that, in FIG. 10*a*, a storage vessel 3, 3', 3" is arranged in the vessel receptacle 64. As can be seen in the two figures, the vessel receptacle 64 is able to move in the Y-direction in the unloading device 60, and for this purpose, a guide 66 extending in the Y-direction is constructed in the same.

The unloading device 60 shown in FIGS. 10a and 10b is designed as a tipping station. For this purpose, the unloading device 60 has two tipping receptacles 63 on the unloading end face 69, which faces the transport device (not illustrated), wherein tipping projections 65 of the vessel receptacle 64 engage in the same. As soon as the tipping projections 65 engage in the tipping receptacles 63 and the vessel receptacle 64 is moved to the discharge end face 69, the tipping movement of the vessel receptacle 64, and thus of the storage vessel 3, 3', 3", is initiated due to the shape of the tipping receptacles 63. So that the storage vessel 3, 3', 3" does not slip or fall from the vessel receptacle 64 when this tipping movement is executed, and during the movement of the vessel receptacle 64 unloading station 60 as such, a retaining device 67 may temporarily fix the storage vessels 3, 3', 3", where the retaining device 67 may be released after the tipping process has been executed, for example. A second identifying device 45 may also be provided on the unloading device 60.

FIG. 10b shows below the vessel receptacle 64 a vessel placement area 64" with an end face 68. Storage vessels 3, 3', 3" are set down in this vessel placement area 64" before they are fixed by the retaining device 67 of the vessel receptacle 64 for transport. The end face 68 of the vessel placement area 64" is, seen vertically, on a level with the leading edge 12 of the shelves 11. As such, the vessel placement area 64" is designed like a storage location, such that storage vessels 3, 3', 3" may be placed on the vessel placement area 64" with the same stock movements which are used to place them on conventional storage locations 5.

Figure 11C:
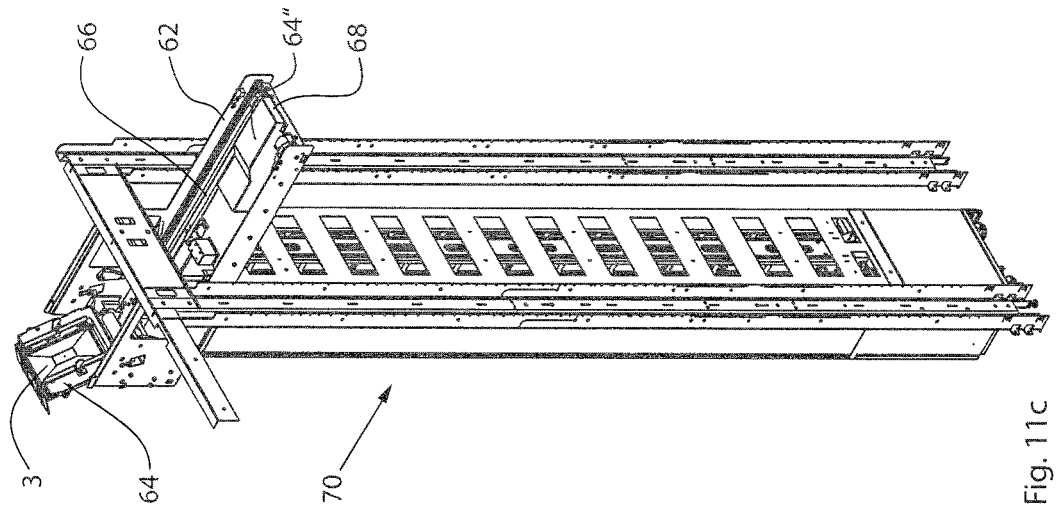
FIG. 11*c* is a perspective partial view of the unloading device/vessel collection device of FIG. 9.
Figure 11B:
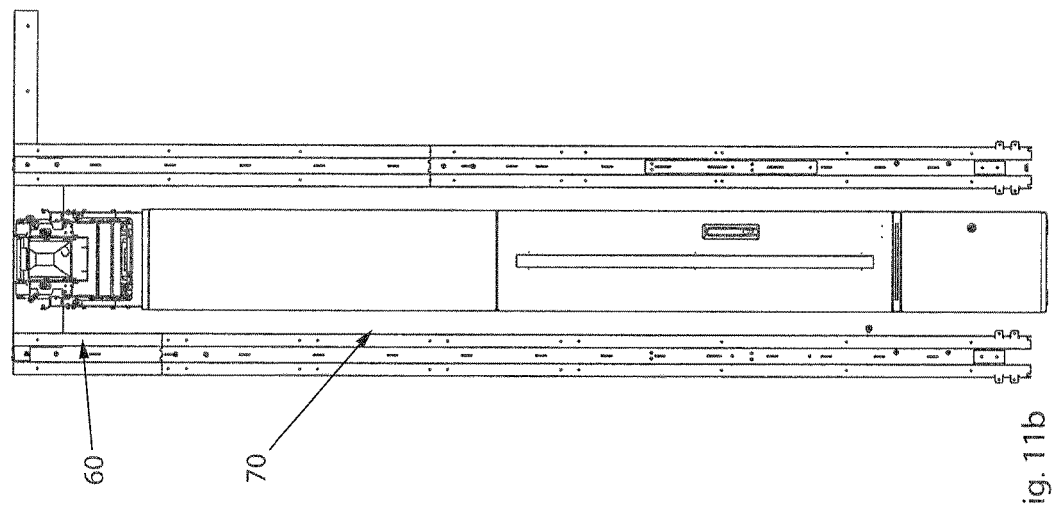
FIG. 11*b* is a front partial view of the unloading device/vessel collection device of FIG. 9.
Figure 11A:
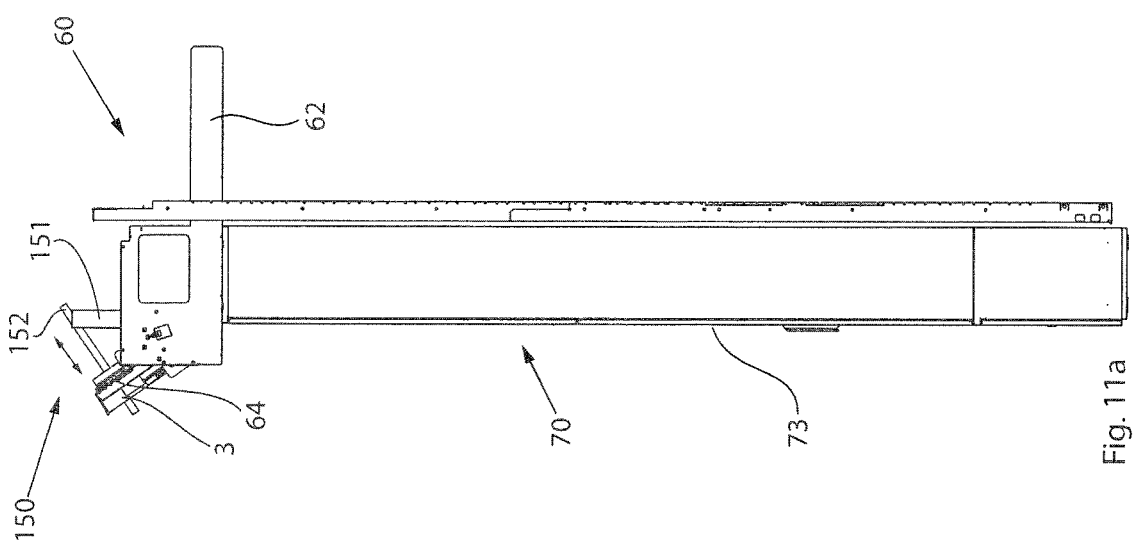
FIG. 11*a* is a side partial view of the unloading device/vessel collection device of FIG. 9.

FIGS. 11a-11c show different views of a combination unloading device 60 and vessel collection device 70. In these figures as well, the vessel collection device 70 is arranged below the section of the unloading device 60, which is arranged outside of the storage device 2, such that storage vessels 3, 3', 3", after being emptied, can be simply transferred down to the vessel collection device 70.

In FIGS. 11a-11c, the vessel receptacle 64 is shown in its emptying position, in which it is moved from the park position which was shown in FIG. 10a. As can be seen particularly in FIG. 11a, the vessel receptacle 64 may be tipped by an interaction of tipping projections (not shown) and tipping receptacles 63, in such a manner that it projects beyond the transport device (not shown). As a result, the drug combinations 4, 4', 4" arranged in storage vessels 3, 3', 3" may be transferred onto the transport device by the tipping movement.

An ejection device 150 may be functionally assigned to the unloading station 60. This includes an ejector 152 with which drug combinations 4, 4', 4" may be ejected from a storage vessel 3, 3', 3" through an opening in the same. A support 151 may connect the ejector 152 with the frame structure 62, for example. A detailed description of a storage vessel 3, 3', 3" that may be used with an ejection device 150, and of the loading and unloading process, is provided in FIGS. 13a-15b.

Figure 12A:
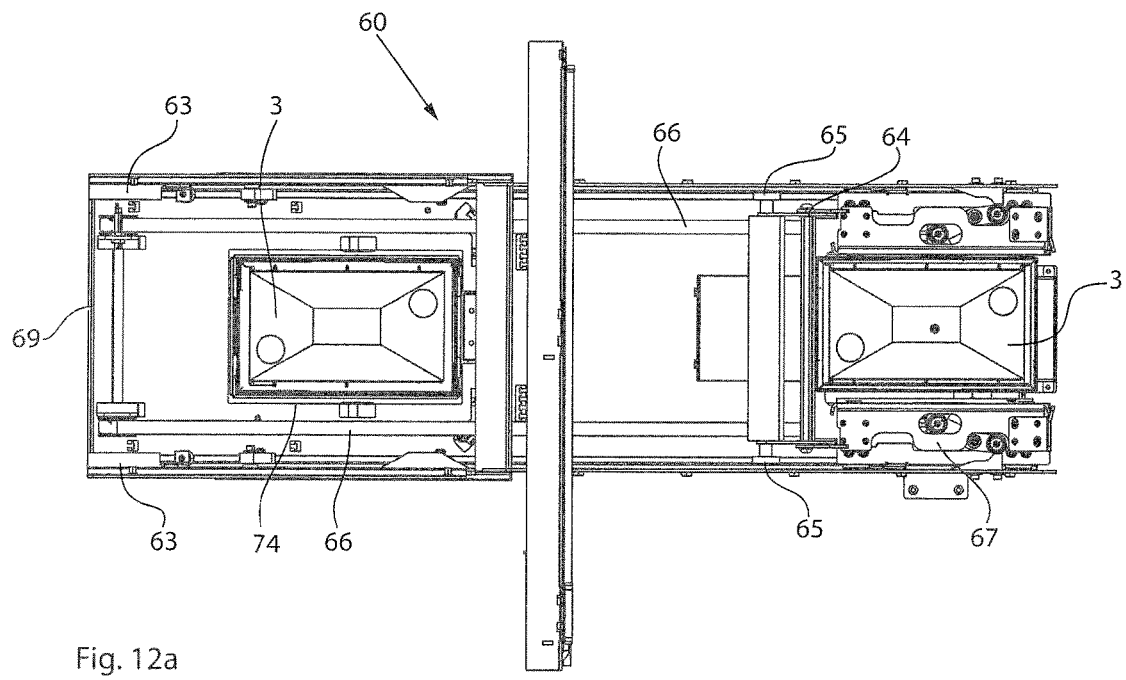
FIGS. 12*a* and 12*b* are top plan views of the unloading device of FIG. 9.
Figure 12B:
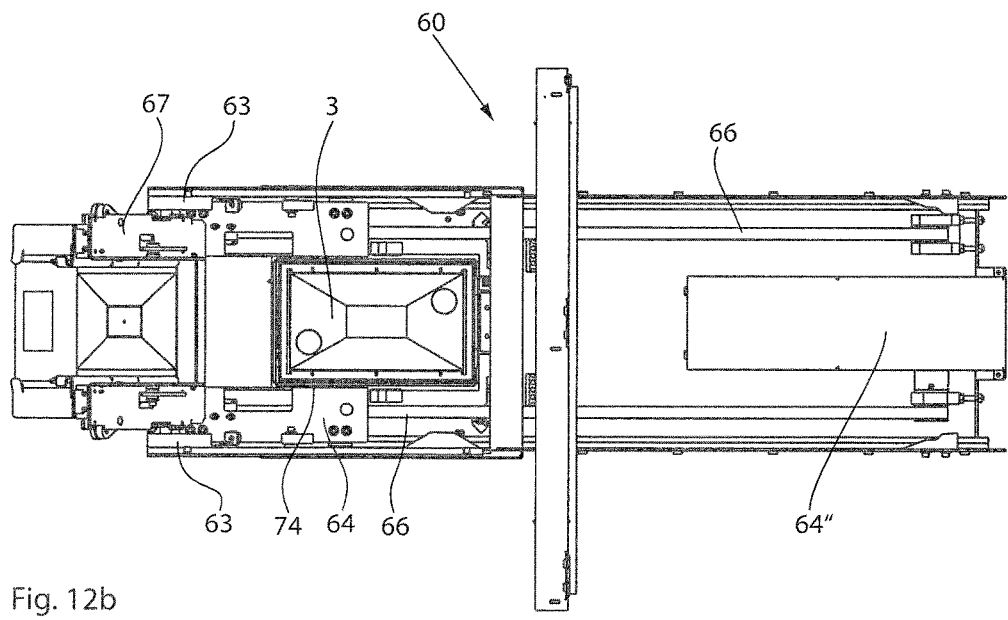

FIGS. 12a and 12b show plan views of the unloading device 60, wherein FIG. 12a shows the vessel receptacle 64 in the park position, and FIG. 12b shows the same in the emptying position. FIG. 12a shows that the storage vessel 3, 3', 3" is fixed by the retaining device 67 of the vessel receptacle 64 for transport.

As can be seen in both figures, the base surface of the frame structure 62 has an opening 74, and the vessel collection device 70 may be arranged below this opening 74. In the two figures, the storage vessel 3, 3', 3" stored in the vessel collection device 70 is seen through the opening 74 below the unloading device 60.

To convey an emptied storage vessel to the vessel collection device 70 after it has been emptied, the vessel receptacle 64 may be moved on the guides 66 over the opening 74 in such a manner that the storage vessel 3, 3', 3" held by the retaining device 67 is arranged over the storage vessels 3, 3', 3" in the vessel collection device 70 and/or the opening 74. Then, the retaining device 67 may be opened, that is the fixation of the storage vessel 3, 3', 3" in the vessel receptacle may be released, such that the emptied storage vessels 3, 3', 3" fall through the opening 74 onto the underlying stack of already-emptied storage vessels 3, 3', 3". In this way, the emptied storage vessels 3, 3', 3" may be conveyed to the vessel collection device 70 particularly easily and quickly. Also, a manner of slide may be constructed below the section of the unloading device 60 that is constructed outside of the storage device 2, conveying emptied storage vessels 3, 3', 3" to a differently-configured vessel collection device.

As mentioned above, the storage vessels 3, 3', 3" may be adapted to the size of the drug combination 4, 4', 4" to achieve the optimum storage capacity of the picking device 1. Depending on the exact configuration, the storage vessels 3, 3', 3" may also be constructed not with a completely cylindrical shape with respect to their height, but rather may have a constriction at the base to enable better stacking of the storage vessels 3, 3', 3".

Figure 13A:
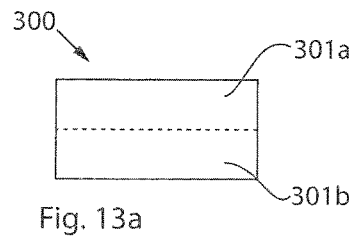
FIG. 13*a* illustrates multiple views of a storage vessel with a base surface that can open.

FIG. 13a shows multiple views of an embodiment of a storage vessel 300, having a lid which is able to open and close, realized by two hinged lid elements (301a, 301b) (see diagram at left), which can temporarily release a discharge opening 310 through which drug combinations 4, 4', 4" may be stocked in and retrieved from the storage vessels 300. The center illustration of FIG. 13a shows the storage vessel 300 from the side, resting on a base surface 302, and having a drug combination 400 shown in the interior. In the illustration at right, the base surface 302 is visible from above and having two openings 303.

The terms "lid" and "base surface" have been selected only for the description of storage vessel 300. Whether the lid is up or down when the box is stocked depends on how the storage vessel 300 is placed on the stocking device and how it is to be unloaded upon retrieval.

Figure 13B:
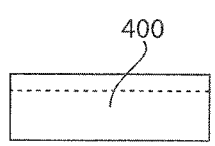
Figure 13B:
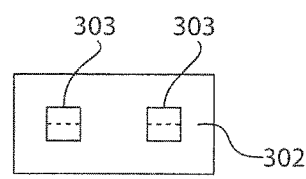
Figure 13B:
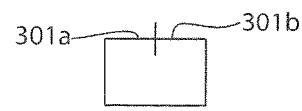

FIGS. 13b and 13c show schematic views of the storage vessel 300 of FIG. 13a during a filling process and an unloading process, wherein each figure shows three illustrated views. In the illustration at left in FIG. 13b, the storage vessel 300 is shown from one end face, resting on the base surface 302. In the center illustration, the cover elements 301a, 301b are open and a drug combination 400 has been inserted. In the illustration at right, the cover elements 301a, 301b have been closed again.

Depending on the unloading device 60 and the design of the lid elements 301a, 301b, storage vessels 300 may be stored lying on the base surface 302. Alternatively, the storage vessels 300 may be rotated after the filling, and stocked lying on the lid. If they are stocked lying on the lid, the base surface 302 may be completely or partly dispensed with. The storage vessel 300 is then designed like a drawer with a releasable floor. For the insertion of a drug combination 400, the storage vessel 300 may then be placed on the closed "lid", and accordingly stocked in this manner as well.

For the retrieval of the drug combination 400 from the storage vessel 300, the lid may be oriented downward, as is shown schematically in the illustration at left in FIG. 13c. For unloading, the "lid" (now the base) may be opened. Due to gravity, the drug combination 400 then falls out of the storage vessel 300. Optionally, the drug combination 400 may be ejected (should the same have become lodged) with a plunger 152 which is guided, for example, through the openings 303. After the unloading, the lid elements 301a, 301b are closed once again.

Corresponding means can be included on the storage vessel 300 itself for the opening/closing of the lid elements 301a, 301b. Alternatively, corresponding means can be included in the unloading device 60.

Figure 14A:
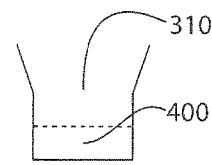
FIGS. 14*a*, 14*b*, 15*a* and 15*b* are schematic views of a gravity unloading station at various stages of an unloading process.
Figure 14A:
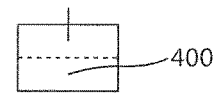
Figure 14A:
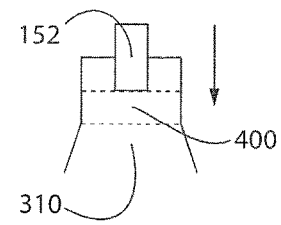
Figure 14A:
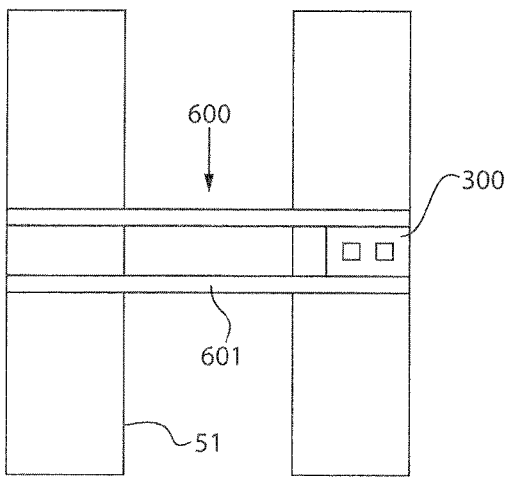
Figure 14B:
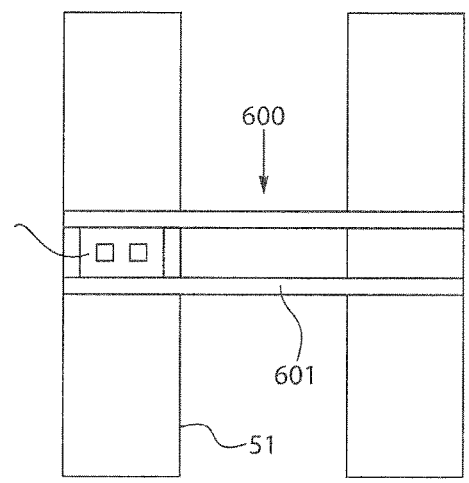

FIGS. 14a, 14b and 15a, 15b show schematic views of a gravity unloading station 600 at different stages of the unloading process. Gravity unloading station 600 may have one or more guides 601 for moving the storage vessel 300. In FIG. 14b, showing the embodiment schematically from above, the storage vessel 300 is in a park position as already described with reference to the above figures. The storage vessel 300 has been placed in this location by the operating device 20.

Figure 15A:
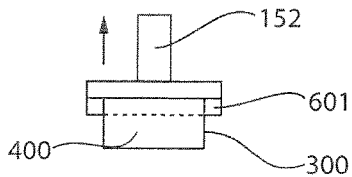
Figure 15B:
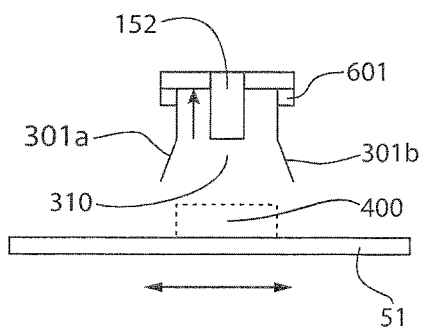

In FIG. 14b, the storage vessel 300 is in the unloading position. In this position, the lid elements 301a, 301b are oriented downwardly, as can be seen in FIG. 15b, which shows the embodiment schematically from the front. Whether the storage vessel 300 had been stocked in this orientation, or has been accordingly oriented by the unloading station 60, is not essential to the disclosure.

After the storage vessel 300 is moved into the unloading position (FIGS. 14b/15a), the lid elements 301a, 302b are opened and the one or more plungers 152 (not shown) are moved through openings 303 to assist the gravity-induced unloading of the drug combination 400 (if this is necessary). Instead of the plunger 152, compressed air could be used, for example. The unloaded drug combination 400 falls onto the transport device 50 and is moved to a delivery station 80.

Figure 16:
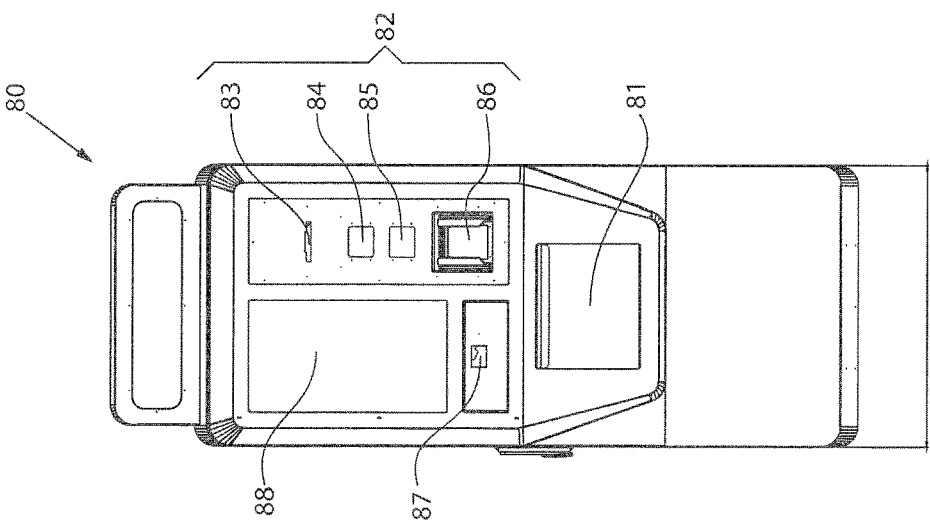
FIG. 16 is a front view of a delivery station.

FIG. 16 shows a delivery station 80 of the picking device 1. The delivery station 80 includes an unloading location 81 and a user interface 82 with multiple components 83-88. Specifically, a receipt printer 83, an RFID reader 84 (for contactless payment), a card feeding means 85 for a conventional card payment, a PIN pad 86 for inputting a numerical code, a bar code scanner 87, and a combined input/display means 88 (e.g., a touch screen). A document scanner (for example for an identification document) and/or a prescription scanner may also be included (not shown).

The aforementioned user interface 82 may include only some of the above components, wherein the exact design of a user interface 82 depends on country specific requirements and the intended use of the delivery station 80 (simple/qualified user). As such, it may be necessary, for example, for the user interface 82 to also have an image capture device (camera) used to take a photo of the user picking up the drug combination 4, 4', 4". Also, all the components for making a payment may be omitted, specifically in cases where drug combinations 4, 4', 4", 400 are provided free of charge. The aforementioned combination of components of the user interface 82 is therefore merely exemplary and illustrative.

Figure 17C:
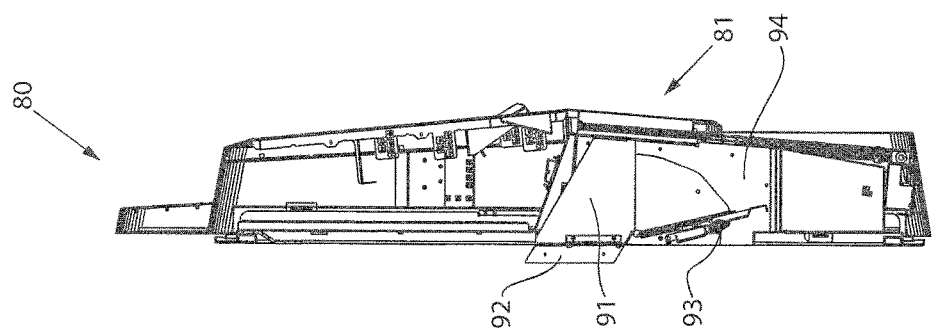
FIGS. 17*a*-17*c* are side views of the delivery station of FIG. 16.
Figure 17B:
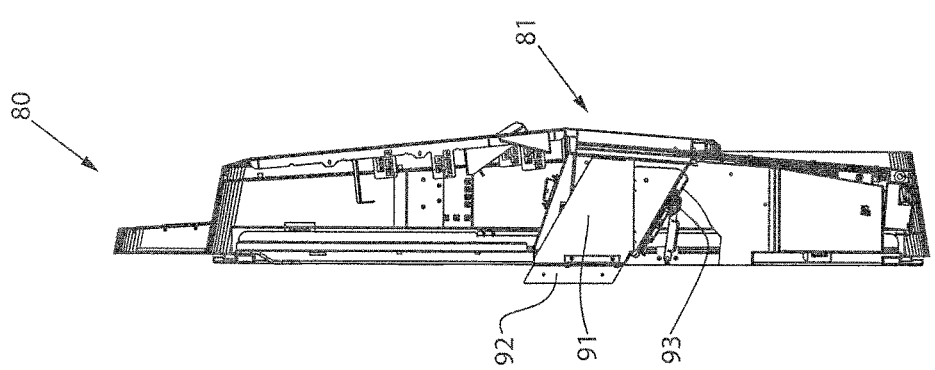
Figure 17A:
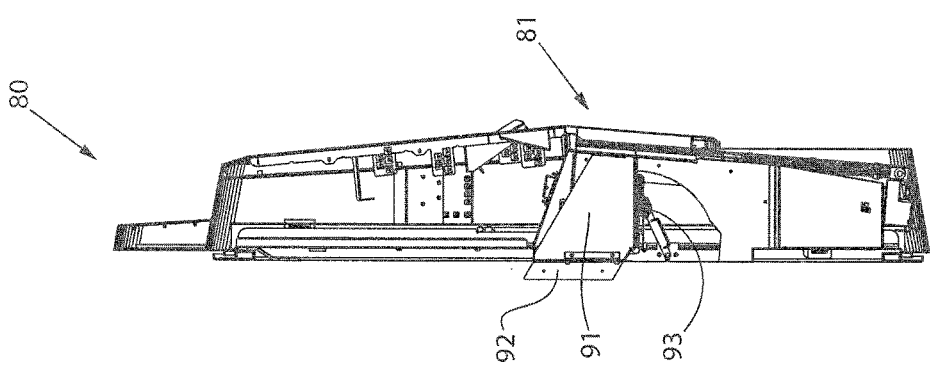

FIGS. 17a-17c show lateral sectional views of the delivery station 80, wherein FIG. 17a to FIG. 17c show the release procedure. The delivery station 80 includes a receiving space 91 coupled via a connector 92 to a transporter (not shown) of the transport device 50. The base 93 of the receiving space 91 may be designed as a releasable flap. Once drug combinations 4, 4', 4", 400 have been conveyed to the receiving space 91 via the transporter, the receiving space 91 may be opened by pivoting the base 93, wherein the drug combination 4, 4', 4", 400 arranged in the receiving space 91 is transferred into a removal space 94 during this process. Such a releasing of the base 93 of the receiving space 91 occurs upon the instruction of the control device 100, specifically once all authentication processes associated with the dispensing process for the drug combination 4, 4', 4", 400 have been completed (see the following description of the method).

The delivery station 80 further includes a return space (not shown) into which drug combinations 4, 4', 4", 400 may be transferred if the authentication process is not successfully completed by the user.

In the following, preferred embodiments of the method according to the invention for the retrieval of drug combinations arranged in storage vessels in a picking device are described.

In the method according to the invention for the retrieval of drug combinations arranged in storage vessels, a drug combination to be retrieved is first identified, specifically by a user providing identification data which uniquely identify a drug combination to be retrieved.

In the event (described below) that the user is a "simple" user, that is, an end customer and/or the addressee of a drug combination, the identification data which identifies a drug combination can be the name of the user, by way of example. The description provided above gives further details on the identification data.

On the basis of the identification data identifying a drug combination, the storage location of the storage vessel in which the identified drug combination is arranged is determined.

In the event that a user has been assigned more than one drug combination, these are may be dispensed together. The user may also be given the option to select, at the delivery station, which drug combinations assigned to him/her will be dispensed. In the following description, it is assumed that a user is only assigned one drug combination.

After the storage location of the storage vessel inside the storage device of the picking device has been determined, the operating device is moved to the storage location assigned to the drug combination to be retrieved and the storage vessel is gripped by the gripper of the operating device. The gripper may include pivotable jaws 27 with which a storage vessel can be pulled from a storage location onto the contact surface of the gripper. Once a storage vessel has been gripped by a gripper and transferred thereto, the operating device and/or the gripper of the operating device is moved to an unloading device 60 and the storage vessel is transferred to a vessel receptacle 64 of the unloading device. The storage vessel may be arranged by the gripper on the vessel placement surface 64" of the unloading device 60, and fixed by the retaining device 67 of the vessel receptacle. The vessel receptacle may also have a depression, for example, into which the storage vessel is moved.

After the storage vessel containing the drug combination to be retrieved has been transferred to the vessel receptacle, the storage vessel is emptied onto the transport device 50. This may be performed by the vessel receptacle being moved out of a park position in which the storage vessel to be emptied is collected into an emptying position in which the storage vessel is emptied (in this case, by tipping).

After the drug combination to be retrieved has been transferred to the transport device, the drug combination is transported by the transport device to a removal location of a delivery station. The removal location is then released upon instructions from a control device coupled to the delivery station, such that the user can remove the drug combination. The release of the removal location is only initiated by the control device if the user has met all authentication requirements. These are governed by national regulations and requirements placed on the drug combination as such. In some countries, a photo of the end user picking up the drug combination may also be made before the same is released. It may be necessary for a document identifying the user, such as an identity card or a passport, to be read to verify the user's identity. A person skilled in the art is aware of numerous other options for enabling and meeting national requirements with regard to the dispensing of drugs.

In the event that the retrieval procedure has been initiated by the user but a step in the authentication has not been completed successfully (e.g., the payment), the drug combination arranged at the removal location 81 may be removed from the removal location so that the delivery station can be used by other users. By way of example, for this purpose, the drug combination may be moved from the removal location into a return space. The retrieval procedure may be initiated only once all of the authentication steps have been performed successfully by the user. In such a case, it is generally unnecessary to make provisions for a removal of a drug combination from the removal location, because the drug combinations are only conveyed to the removal location if all the authentication steps have been successfully carried out.

An advantage of the picking device and the method according to the disclosure is that the picking device can comprise a multiple delivery stations which can be arranged in different spatial configurations. As such, it can be contemplated, for example, that the picking device has three delivery stations, wherein one is used by a qualified user such as a pharmacist, and the two remaining delivery stations are used by simple users. In this case, one of the two delivery stations is positioned within the premises of a pharmacy, and the remaining delivery station is positioned outside the premises in which the storage device of the picking device is arranged. Such a delivery station arranged outside the premises of the storage device may be designed in the form of a drive-through station, by way of example.

The storage vessels emptied onto the transport device may be conveyed to a vessel collection device, which may be constructed below the unloading device, for example. By way of example, the retaining device of the vessel receptacle may be released for this purpose, such that the storage vessel can fall due to gravity through an opening in a base surface of the unloading station into a storage space of the vessel collection device. A slide may be functionally assigned to the unloading device, wherein the emptied storage vessels may be conveyed by said slide either to the vessel collection device or to a vessel provision device. The emptied storage vessels may be moved back into the park position after the emptying process, gripped by the operating device, and either conveyed to the vessel provision device or simply moved to an empty storage location. Which of the aforementioned options are carried out depends on how high the retrieval requirements are.

The present disclosure is provided to enable any person skilled in the art to practice the various aspects described herein. The disclosure provides various examples of the subject technology, and the subject technology is not limited to these examples. For example, any or all of the elements or components in this disclosure may by combined in different ways. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the subject technology.

The word "exemplary" or the term "for example" is used herein to mean "serving as an example or illustration." Any aspect or design described herein as "exemplary" or "for example" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A picking device for dispensing drug combinations arranged in storage vessels, comprising:
    at least one storage device comprising having a plurality of storage locations for storage vessels;
    an operating device configured to be moved horizontally and vertically in front of a row of shelves, the operating device coupled to a control device;
    at least one stocking device configured to move storage vessels for drug combinations into the storage device, wherein the operating device is configured to remove the storage vessels therefrom;
    at least one first identifying device for identifying the drug combinations;
    an unloading device;
    at least one delivery station coupled to the control device, the delivery station comprising a removal location and a user interface; and
    a transport device, coupled to the control device, configured to transfer drug combinations from the unloading device, wherein the transport device connects the storage device to each of the at least one delivery stations, and wherein any of the drug combinations is deliverable to any of the at least one delivery stations.

2. The picking device of claim 1, wherein the unloading device comprises a vessel receptacle having a design corresponding to that of a storage location, such that the storage vessels are configured to be deposited by the operating device in the vessel receptacle.

3. The picking device of claim 1, wherein the unloading device is a gravity unloading station by which drug combinations arranged in one of the storage vessels are transferred to the transport device at a receiving location via a discharge opening of the storage vessel.

4. The picking device of claim 3, wherein the unloading device is a tipping station wherein drug combinations arranged in one of the storage vessels are tipped onto the transport device at a receiving location via the discharge opening of the storage vessel.

5. The picking device of claim 1, wherein the unloading device comprises an ejection device configured to eject drug combinations arranged in one of the storage vessels onto the transport device at a receiving location via the discharge opening of the storage vessel.

6. The picking device of claim 1, wherein the unloading device comprises a movable vessel receptacle configured to receive storage vessels to be emptied when in a park position, and to move the storage vessels to be emptied to an emptying position.

7. The picking device of claim 4, wherein the movable vessel receptacle comprises a retaining device configured to hold storage vessels in a temporary manner for later detachment.

8. The picking device of claim 1, wherein a vessel collection device is functionally assigned to the unloading device and is configured to receive emptied storage vessels from the unloading device.

9. The picking device of claim 6, wherein the vessel collection device is arranged below the unloading device, wherein emptied storage vessels are configured to be fed to the vessel collection device by releasing the retaining device.

10. The picking device of claim 6, wherein the vessel collection device comprises an access opening accessible from outside the storage device for removal of collected storage vessels.

11. The picking device of claim 1, wherein the storage device comprises a delivery device arranged at least partially within the radius of action of the operating device and which is accessible from outside of the storage device.

12. The picking device of claim 1, further comprising a vessel provision device accessible from outside the storage device and configured for emptied storage vessels.

13. The picking device of claim 1, further comprising at least two delivery stations configured for different types of access for different users.

14. The picking device of claim 11, wherein one of the delivery stations is configured to be operated from outside of a building in which the storage device is arranged.

15. The picking device of claim 1, further comprising a second identifying device configured to identify drug combinations prior to the emptying of the storage vessels in the unloading device.

16. A method for retrieving drug combinations arranged in storage vessels in a picking device, the method comprising:
    a) identifying a drug combination to be retrieved, comprising:
        providing, by a user, uniquely identifying identification data for the drug combination to be retrieved; and
        determining a storage location inside the picking device assigned to the drug combination to be retrieved;

b) moving an operating device to the assigned storage location of the drug combination;

c) gripping, by the operating device, a storage vessel arranged at the assigned storage location, the storage vessel containing the drug combination, and transferring the storage vessel to a vessel receptacle of an unloading device;

d) emptying the transferred storage vessel onto the transport device;

e) transporting, by the transport device, the drug combination to a removal location of a delivery station; and f) clearing the removal location of the drug combination upon instructions from a control device coupled to the delivery station.

17. The method of claim 16, wherein the vessel receptacle is arranged prior to the transfer of the storage vessel in such a manner that the operating device transfers the storage vessel with conventional stocking movements.

18. The method of claim 16, wherein the storage vessel is emptied by the vessel receptacle being tipped so that drug combinations fall onto the transport device.

19. The method of claim 16, wherein the vessel receptacle is moved from a park position into an emptying position prior to the emptying of the storage vessel.

20. The method of claim 16, wherein the storage vessel is moved following the emptying thereof into a vessel collection device or a vessel provision device.

21. The method of claim 16, wherein a drug combination to be retrieved is identified by personal data of a user being provided as the identification data and evaluated.

22. The method of claim 21, wherein, if more than one drug combination is assigned to a user, the user is given the option of selecting the drug combinations to be dispensed.

23. The method of claim 16, wherein the steps of the method for the retrieval following step a) are only carried out if all user actions associated with the dispensing have been performed successfully.

24. The method of claim 16, wherein a drug combination arranged in a storage vessel is identified by the second identifying device prior to the emptying of the storage vessel, and the storage vessel is only emptied onto the transport device if the identified drug combination corresponds to the drug combination identified by the identification data.

25. The method of claim 24, wherein, if the identified drug combination does not correspond to the drug combination identified by the identification data, the same is removed from the stock of the storage device.

* * * * *